(12) United States Patent
Zhen et al.

(10) Patent No.: US 11,293,914 B2
(45) Date of Patent: Apr. 5, 2022

(54) CHEMICAL SENSORS WITH NON-COVALENT, ELECTROSTATIC SURFACE MODIFICATION OF GRAPHENE

(71) Applicants: REGENTS OF THE UNIVERSITY OF MINNESOTA, Minneapolis, MN (US); Boston Scientific Scimed, Inc., Maple Grove, MN (US)

(72) Inventors: Xue Zhen, Minneapolis, MN (US); Philippe Pierre Joseph Buhlmann, Minneapolis, MN (US); Steven J. Koester, Edina, MN (US); Justin Theodore Nelson, Minneapolis, MN (US)

(73) Assignees: Boston Scientific Scimed, Inc., Maple Grove, MN (US); REGENTS OF THE UNIVERSITY OF MINNESOTA, Minneapolis, MN (US)

(*) Notice: Subject to any disclaimer, the term of this patent is extended or adjusted under 35 U.S.C. 154(b) by 176 days.

(21) Appl. No.: 16/393,177

(22) Filed: Apr. 24, 2019

(65) Prior Publication Data
US 2019/0331661 A1 Oct. 31, 2019

Related U.S. Application Data

(60) Provisional application No. 62/662,305, filed on Apr. 25, 2018.

(51) Int. Cl.
*G01N 33/497* (2006.01)
*G01N 27/22* (2006.01)
*G01N 27/12* (2006.01)

(52) U.S. Cl.
CPC ......... *G01N 33/497* (2013.01); *G01N 27/125* (2013.01); *G01N 27/227* (2013.01); *G01N 2610/00* (2013.01)

(58) Field of Classification Search
CPC .. G01N 27/125; G01N 27/227; G01N 33/497; G01N 2610/00
See application file for complete search history.

(56) References Cited

U.S. PATENT DOCUMENTS 8,294,135 B2 10/2012 Lebedev et al.
8,581,262 B2 11/2013 Pan et al.
(Continued)

FOREIGN PATENT DOCUMENTS

CA 2673142 4/2008
CA 2800887 12/2011
(Continued)

OTHER PUBLICATIONS

Hasobe, "Photo- and electro-functional self-assembled architectures of porphyrins", Physics Chemistry Chemical Physics, 2012, 14, pp. 15975-15987 (Year: 2012).*

(Continued)

*Primary Examiner* — Matthew D Krcha
*Assistant Examiner* — Austin Q Le
(74) *Attorney, Agent, or Firm* — Pauly, DeVries, Smith & Deffner LLC

(57) ABSTRACT

Embodiments include chemical sensors, devices and systems including the same, and related methods. In an embodiment, a medical device is provided. The medical device can include a graphene varactor, including a graphene layer and a self-assembled monolayer disposed on an outer surface of the graphene layer through electrostatic interactions between a partial positive charge on hydrogen atoms of one or more hydrocarbons of the self-assembled monolayer and a π-electron system of graphene. The self-assembled monolayer can include one or more substituted porphyrins or substituted metalloporphyrins, or derivatives thereof. Other embodiments are also included herein.

9 Claims, 7 Drawing Sheets

(56) References Cited

U.S. PATENT DOCUMENTS

| | | |
|---|---|---|
| 8,951,473 B2 | 2/2015 | Wang et al. |
| 8,961,830 B2 | 2/2015 | Reynolds et al. |
| 9,011,779 B1 | 4/2015 | Anglin, Jr. et al. |
| 9,085,715 B2 | 7/2015 | Berthelot et al. |
| 9,267,908 B2 | 2/2016 | Wang et al. |
| 9,366,664 B2 | 6/2016 | Anglin, Jr. et al. |
| 9,410,040 B2 | 8/2016 | Li et al. |
| 9,513,244 B2 | 12/2016 | Koester |
| 9,671,392 B2 | 6/2017 | Jeppsen et al. |
| 9,689,836 B2 | 6/2017 | Makaram et al. |
| 9,775,241 B2 | 9/2017 | Walczak et al. |
| 9,859,034 B2 | 1/2018 | Sjong |
| 11,079,371 B2 | 8/2021 | Zhen et al. |
| 2009/0104435 A1 | 4/2009 | Hutchison et al. |
| 2012/0058350 A1 | 3/2012 | Long et al. |
| 2012/0214172 A1 | 8/2012 | Chen et al. |
| 2015/0298115 A1 | 10/2015 | Campidelli et al. |
| 2015/0338390 A1 | 11/2015 | Anglin et al. |
| 2016/0093806 A1 | 3/2016 | Turchanin |
| 2016/0289769 A1 | 10/2016 | Schwartz et al. |
| 2016/0334386 A1 | 11/2016 | Anglin et al. |
| 2016/0356741 A1 | 12/2016 | Makaram et al. |
| 2017/0212116 A1 | 7/2017 | Braga et al. |
| 2017/0307576 A1* | 10/2017 | Anglin, Jr. ......... G01N 33/0059 |
| 2019/0025237 A1 | 1/2019 | Kelly et al. |
| 2019/0257825 A1 | 8/2019 | Zhen et al. |
| 2020/0166435 A1 | 5/2020 | Sherwood et al. |
| 2020/0191737 A1 | 6/2020 | Sherwood et al. |
| 2021/0057526 A1 | 2/2021 | Zhen et al. |
| 2021/0072208 A1 | 3/2021 | Sherwood et al. |
| 2021/0356457 A1 | 11/2021 | Zhen et al. |
| 2021/0369250 A1 | 12/2021 | Buhlmann et al. |

FOREIGN PATENT DOCUMENTS

| | | |
|---|---|---|
| CN | 102183557 | 9/2011 |
| CN | 103950920 | 7/2014 |
| CN | 103852505 | 11/2015 |
| CN | 103877574 | 1/2016 |
| CN | 105688995 | 6/2016 |
| CN | 107180706 | 9/2017 |
| EP | 3431977 | 1/2019 |
| IN | 201627028955 | 10/2016 |
| JP | H0682455 | 3/1994 |
| JP | 2012122814 | 6/2012 |
| JP | 5837058 | 11/2015 |
| KR | 20170057001 | 5/2017 |
| KR | 101797737 | 11/2017 |
| WO | 2011158068 | 12/2011 |
| WO | 2012135565 | 10/2012 |
| WO | 2012138632 | 10/2012 |
| WO | 2015179623 | 11/2015 |
| WO | 2016145300 | 9/2016 |
| WO | 2017066583 | 4/2017 |
| WO | 2017095922 | 6/2017 |

OTHER PUBLICATIONS

Giancane et al., "State of art in porphyrin Langmuir-Blodgett films as chemical sensors", Advances in Colloid and Interface Science, 2012, vol. 171-172, pp. 17-35 (Year: 2012).*

Allen, Matthew J. et al., "Honeycomb Carbon: A Review of Graphene," Chem. Rev. 2010, 110, 132-145 (14 pages).

An, Xiaohong et al., "Stable Aqueous Dispersions of Noncovalently Functionalized Graphene from Graphite and their Multifunctional High-Performance Applications," Nano Lett. 2010, 10, 4295-4301 (7 pages).

Bair, Kenneth W. et al., "(1-Pyrenylmethyl)amino Alcohols, a New Class of Antitumor DNA intercalators. Discovery and Initial Amine Side Chain Structure-Activity Studies," J. Med. Chem. 1990, 33, 2385-2393 (9 pages).

Bard, Allen J. et al., "Electrochemical Methods: Fundamentals and Applications," Wiley New York: 1980; vol. 2 (850 pages).

Biedermann, Frank et al., "Experimental Binding Energies in Supramolecular Complexes," Chem. Rev. 2016, 116(9), 5216-5300 (85 pages).

Bock, Harald et al., "Helicenes from Diarylmaleimides," Organic Letters 2014, 16, 1546-1549 (5 pages).

Boeseken, J. "The Use of Boric Acid for the Determination of the Configuration of Carbohydrates," Adv. Carbohydr. Chem. 1949, 4, 189-210 (22 pages).

Cao, Mengmei et al., "Electrochemical and Theoretical Study of π-π stacking Interactions between Graphitic Surfaces and Pyrene Derivatives," J. Phys. Chem. C 2014, 118(5), 2650-2659 (10 pages).

Chamberlain Ii, Richard V. et al., "Electrostatically-induced Inclusion of Anions in Cyclodextrin Monolayers on Electrodes," Langmuir 2000, 1388-1396 (9 pages).

Cheng, Zengguang et al., "Suspended Graphene Sensors with Improved Signal and Reduced Noise," Nano Lett. 2010, 10, 1864-1868 (5 pages).

Connors, Kenneth A. et al., "The Stability of Cyclodextrin Complexes in Solution," Chem. Rev. 1997, 97, 1325-1357 (34 pages).

Deen, David A. et al., "Graphene-based quantum capacitance wireless vapor sensors," IEEE Sens. J. 2014, 31(7), 1405-1411 (8 pages).

Di Natale, Corrado et al., "Lung Cancer Identification by the Analysis of Breath by Means of an Array of Non-Selective Gas Sensors," Biosensors and Bioelectronics 18 (2003) 1209-1218 (10 pages).

Ebrish, M.A. et al., "Operation of multi-finger graphene quantum capacitance varactors using planarized local bottom gate electrodes," Applied Physics Letters 2012, 100 (14), 143102 (4 pages).

Ebrish, Mona A. et al., "Effect of Noncovalent Basal Plane Functionalization of the Quantum Capacitance in Graphene," ACS Appl. Mater. Interfaces 2014, 6, 10296-10303 (8 pages).

Elemans, Johannes A. et al., "Molecular Materials by Self-Assembly of Porphyrins, Phthalocyanines, and Perylenes," Adv. Mater. 2006, 18, 1251-1266 (16 pages).

Fogel, Yulia et al., "Graphitic Nanoribons with Dibenzo[e,l]pyrene Repeat Units: Synthesis and Self-Assembly," Macromolecules 2009, 42, 6878-6884 (7 pages).

Gautam, Madhav et al., "Gas sensing properites of graphene synthesized by chemical vapor deposition," Materials and Science Engineering C31 (2011) 1405-1411 (7 pages).

Georgakilas, Vasilios et al., "Functionalization of Graphene: Covalent and Non-Covalent Approaches, Derivatives and Applications," Chem. Rev. 2012, 112(11), 6156-6214 (59 pages).

Georgakilas, Vasilios et al., "Noncovalent Functionalization of Graphene and Graphene Oxide for Energy Materials, Biosensing, Catalytic, and Biomedical Applications," Chem. Rev. 2016, 116, 5464-5519 (56 pages).

Ghosh, Sujoy et al., "Effect of 1-Pyrene Carboxylic-Acid Functionalization of Graphene on Its Capacitive Energy Storage," J. Phys. Chem. C 2012, 116, 20688-20693 (6 pages).

Good, Robert J. "Contact angle, wetting, and adhesion: a critical review," J. Adhesion Sci. Technol. 1992, vol. 6, No. 12, pp. 1269-1302 (34 pages).

Gorodetsky, Alon A. et al., "Electrochemistry Using Self-assembled DNA Monolayers on Highly Oriented Pyrolytic Graphite," Langmuir 2006, 22, 7917-7922 (6 pages).

Guo, Yujing et al., "Cyclodextrin Functionalized Graphene Nanosheets with High Supramolecular Recognition Capability: synthesis and Host-Guest Inclusion for Enhanced Electrochemical Performance," ACS Nano, 2010, abstract only (2 pages).

Guo, Zanru et al., "Light-Switchable Single-Walled Carbon Nanotubes Based on Host-Guest Chemistry," Adv. Funct. Mater. 2013, 23, 5010-5018 (18 pages).

Hill, Ernie W. et al., "Graphene Sensors," IEEE Sensors Journal, vol. 11, No. 12, Dec. 2011 (10 pages).

Hinnemo, Malkolm et al., "On Monolayer Formation of Pyrenebutyric Acid on Graphene," Langmuir, 2017, vol. 33, No. 14 pp. 3588-3593 (6 pages).

Hsiao, Min-Chien et al., "Preparation and properties of a graphene reinforced nanocomposite conducting plate," J. Mater. Chem., 2010, 20, 8496-8505 (10 pages).

(56) References Cited

OTHER PUBLICATIONS

Hsieh, Chien-Te et al., "Field emission from various CuO nanostructures," Applied Physics Letters 2003, vol. 83, No. 6 (3 pages).
Huang, Ke-Jing et al., "Novel electrochemical sensor based on functionalized graphene for simultaneous determination of adenine and guanine in DNA," Colloids and Surfaces B: Biointerfaces 82 (2011) 543-549 (7 pages).
Hunter, Christopher A. et al., "The Nature of π-π Interactions," J. Am. Chem. Soc. 1990, 112, 5525-5534 (10 pages).
"International Search Report and Written Opinion," for PCT Application No. PCT/US2019/018741 dated May 6, 2019 (17 pages).
Jiao, Dezhi et al., "Supramolecular Peptide Amphiphile Vesicles through Host-Guest Complexation," Angew. Chem. Int. Ed. 2012, 51, 9633-9637 (5 pages).
Josef, Szejtli "Introduction and General Overview of Cyclodextrin Chemistry," Chem. Rev. 1998, 98, 1743-1753 (12 pages).
Kang, Xinhuang et al., "Glucose Oxidase-graphene-chitosan modified electrode for direct electrochemistry and glucose sensing," Biosensors and Bioelectronics 25 (2009) 901-905 (5 pages).
Koester, Steven J. "High Quality Factor Graphene Varactors for Wireless Sensing Applications," Applied Physics Letters 99, 163105 (2011), 3 pages.
Kozbial, Andrew et al., "Study on the surface energy of graphene by contact angle measurement," Langmuir 2014, 30 (28), 8598-8606 (28 pages).
Kuila, Tapas et al., "Chemical functionalization of graphene and its applications," Progress in Materials Science 57 (2012) 1061-1105 (45 pages).
Lauffer, Peter et al., "Molecular and electronic structure of PTCDA on bilayer graphene on SiC(0001) studied with scanning tunnerling microscopy," Phys. Stat. Sol. (b) 2008, 245, No. 10, 2064-2067 (4 pages).
Lechner, Christoph et al., "Adhesive Forces Between Aromatic Molecules and Graphene," The Journal of Physical Chemistry C 2014, 118(36), 20970-20981 (12 pages).
Lecourt, Thomas et al., "Triisobutylaluminium and Diisobutylaluminium Hydride as Molecular Scalpels: The Regioselective Stripping of Perbenzylate Sugars and Cyclodextrins," Chem. Eur. J. 2004, 10, 2960-2971 (12 pages).
Liu, Yuxin et al., "Biological and Chemical Sensors based on Graphene Materials," Chem. Soc. Rev. 2012, 41 (6), 2283-2307 (27 pages).
Loh, Kian P. et al., "The Chemistry of Graphene," J. Mater. Chem., 2010, 20, 2277-2289 (13 pages).
Long, Brenda et al., "Non-Covalent Functionalization of Graphene Using Self-Assembly of Alkane-Amines," Adv. Funct. Mater. 2012, 22, 717-725 (9 pages).
Lu, Chun-Hua et al., "A Graphene Platform for Sensing Biomolecules," Angew. Chem. Int. Ed. 2009, 48, 4785-4787 (3 pages).
Machado, Roberto F. et al., "Detection of Lung Cancer by Sensor Array Analyses of Exhaled Breath," Am J Respir Crit Care Med, vol. 171, 1286-1291 (2005), 6 pages.
Mann, Jason A. et al., "Improving the Binding Characteristics of Tripodal Compounds on Single Layer Graphene," American Chemical Society 2013, vol. 7, No. 8, 7193-7199 (7 pages).
Manochehry, Sepehr et al., "Optical biosensors utilizing graphene and functional DNA molecules," J. Mater. Res. 2017, 32(15), 2973-2983 (11 pages).
Mao, Shun et al., "Specific Protein Detection Using Thermally Reduced Graphene Oxide Sheet Decorated with Gold Nanoparticle-Antibody Conjugates," Adv. Mater. 2010, 22, 3521-3526 (6 pages).
Nag, Sanada et al., "Ultrasensitive QRS made by supramolecular assembly of functionalized cyclodextrins and graphene for the detection of lung cancer VOC biomarkers," Journals of Materials Chemistry B 2014, 2, pp. 6571-6579 (9 pages).
Ohno, Yasuhide et al., "Electrolyte-Gated Graphene Field-Effect Transistors for Detecting pH and Protein Adsorption," Nano Letters 2009, vol. 9, No. 9, 3318-3322 (5 pages).
Olson, Eric J. et al., "Capacitive Sensing of Intercalated H20 Molecules Using Graphene," ACS Appl. Mater. Interfaces 2015, 7(46), 25804-25812 (29 pages).
Olson, Eric J. et al., "Getting More out of a Job Plot: Determination of Reactant to Product Stoichiometry in Cases of Displacement Reactions and n:n Complex Formation," J. Org. Chem. 2011, 76, 8406-8412 (7 pages).
Pathipati, Srinivasa R. et al., "Modulation of charge transport properties of reduced graphene oxide by submonolayer physisorption of an organic dye," Organic Electronics 14 (2013) 1787-1792 (6 pages).
Peressi, Maria "Surface Functionalization of Graphene," Graphene Chemistry, John Wiley & Sons, Ltd:2013, pp. 233-253 (21 pages).
Poulston, S. et al., "Surface Oxidation and Reduction of CuO and Cu2O Studied Using XPS and XAES," Surface and Interface Analysis, vol. 24, 811-820 (10 pages).
Putta, Chandrababu et al., "Palladium Nanoparticles on Beta-Cyclodextrin Functionalised Graphene Nanosheets: a Supramolecular Based Heterogeneous Catalyst for C-C Coupling Reactions under Green Reaction Conditions," RSC Adv., 2015, 5, 6652-6660 (9 pages).
Rekharsky, Mikhail V. et al., "Complexation Thermodynamics of Cyclodextrins," Chem. Rev. 1998, 98, 1875-1917 (44 pages).
Reuillard, B et al., "Non-covalent double functionalization of carbon nanotubes wiht a NADH oxidation Ru(II)-based molecular catalyst and a NAD-dependent glucose dehydrogenase," Chem. Commun. 2014, 50(79), 11731-11734 (5 pages).
Rojas, Maria T. et al., "Supported Monolayers Containing Preformed Binding-Sites—Synthesis and Interfacial Binding-Properties of a Thiolated Beta-Cyclodextrin Derivative," J. Am. Chem. Soc. 1995, 117, 336-343 (8 pages).
Schedin, F. et al., "Detection of Individual Gas Molecules Adsorbed on Graphene," Nat. Mater. 2007, 6(9), 652-655 (11 pages).
Shao, Yuyan "Graphene Based Electrochemical Sensor and Biosensors: A Review," Electroanalysis 2010, 22, No. 10, 1027-1036 (10 pages).
Shao, Yuyan et al., "Nitrogen-doped graphene and its electrochemical applications," J. Mater. Chem., 2010, 20, 7491-7496 (6 pages).
Swanson, Emily et al., "Self Assembly of Monolayers on Grpahene with Pyrene and Cyclodextrin Derivatives," Research Poster. Elon University, LANDO program, Research Experience for Undergraduates Program of the National Science Foundation, Council of Undergraduate Research Experiences for Undergraduates symposium in Washington, D.C., Oct. 23-24, 2016 (1 page).
Terse-Thakoor, Trupti et al., "Graphene based biosensors for healthcare," J. Mater. Res. 2017, 32(15), 2905-2929 (25 pages).
Vincent, Mark A. et al., "Accurate Prediction of Adsorption Energies on Graphene, Using a Dispersion-Corrected Semiempirical Method Including Solvation," J. Chem. Inf. Model. 2014, 54, 2225-2260 (6 pages).
Wang, Lihua "A novel [beta]-cyclodextrin Functionalized Reduced Graphene Oxide Electrochemical Sensor for Blood Glucose Detection," International Journal of Electrochemical Science, Dec. 28, 2017 pp. 1594-1602 (9 pages).
Wang, Qing Hua et al., "Room-temperature molecular-resolution characterization of self-assembled organic monolayers on epitaxial graphene," Nature Chemistry 2009 vol. 1 (3), 206-211 (6 pages).
Wayu, Mulugeta B. et al., "Electropolymerization of Beta-Cyclodextrin onto Multi-Walled Carbon Nanotube Composite Films for Enhanced Selective Detection of Uric Acid," Journal of Electroanalytical Chemistry 783 (2016), 192-200 (9 pages).
Xi, Yuxi et al., "Flexible Graphene Films via te Filtration of Water-Soluble Noncovalent Functionalized Graphene Sheets," J. Am. Chem. Soc. 2008, 130, 5856-5857 (2 pages).
Xu, Huifeng et al., "Direct Electrochemixtry and electrocatalysis of hemoglobin protein entrapped in graphene and chitosan composite film," Talanta 81 (2010) 334-338 (5 pages).
Yavari, Fazel et al., "Graphene-Based Chemical Sensors," J. Phys. Chem. Lett. 2012, 3, 1746-1753 (8 pages).
Zhang, Yao et al., "Capacitive Sensing of Glucose in Electrolytes using Graphene Quantum Capacitance Varactors," ACS Appl. Mater. Interfaces 2017, 9, 38863-38869 (7 pages).

(56) References Cited

OTHER PUBLICATIONS

Zhang, Yao et al., "Glucose Sensing with Graphene Varactors," IEEE Sensors, Sensors 2016—Proceedings, Orlando, FL 2016 (3 pages).
Zhang, Yiheng et al., "Direct Measurements of the Interaction between Pyrene and Graphite in Aqueous Media by Single Molecule Force Spectroscopy: Understanding the π-π Interactions," Langmuir 2007, 23, 7911-7915 (5 pages).
Zhao, Yan-Li et al., "Noncovalent Functionalization of Single-Walled Carbon Nanotubes," Accounts of Chemical Research 2009, vol. 42, No. 8. 1161-1171 (12 pages).
Zhen, Xue et al., "Noncovalent Monolayer MOdification of Graphene Using Pyrene and Cyclodextrin Receptors for Chemical Sensing," ACS Applied Nano Materials 2018, vol. 1, No. 6 pp. 2718-2726 (9 pages).
Zhu, Yanwu et al., "Graphene and Graphene Oxide: Synthesis, Properties, and Applications," Adv. Mater. 2010, 22, 3906-3924 (19 pages).
Brust, Mathias et al., "Novel Gold-Dithiol Nano-Networks with Non-Metallic Electronic Properties," Adv. Mater. 1995, 7, No. 9 795-797 (3 pages).
Brust, Mathias et al., "Synthesis of Thiol-derivatised Gold Nanoparticles in a Two-phase Liquid-Liquid System," J. Chem. Soc., Chem. Commun., 1994, 801-802 (2 pages).
"First Examination Report," for Australian Patent Application No. 2019224011 dated Apr. 9, 2021 (4 pages).
"International Search Report and Written Opinion," for PCT Application No. PCT/US2020/046829 dated Nov. 18, 2020 (15 pages).
Li, Errui et al., "Aliphatic Aldehyde Detection and Adsorption by Nonporous Adaptive Pillar[4]arene[1]quinone Crystals with Vapochromic Behavior," ACS Applied Materials & Interfaces, 2018, 10, 23147-23153 (23 pages).
"Non-Final Office Action," for U.S. Appl. No. 16/280,635 dated Feb. 10, 2021 (40 pages).
"Notice of Allowance," for U.S. Appl. No. 16/280,635 dated Mar. 31, 2021 (14 pages).
Peng, Gang et al., "Diagnosing lung cancer in exhaled breath using gold nanoparticles," Nature nanotechnology, 2009, 4(10), 669-673 (5 pages).
"Response to Communication Pursuant to Rules 161(1) and 162 EPC," for European Patent Application No. 19709268.7 filed Apr. 1, 2021 (12 pages).
"Response to Non-Final Rejection," dated Feb. 10, 2021 for U.S. Appl. No. 16/280,635, submitted via EFS-Web on Mar. 17, 2021, 16 pages.
Rodner, Marius et al., "Graphene Decorated with Iron Oxide Nanoparticles for Highly Sensitive Interaction with Volatile Organic Compounds," Sensors 2019, 19, 918-026 (9 pages).
Song, Nan et al., "Applications of pillarenes, an emerging class of synthetic macrocycles," Science China Chemistry, 2014, 57(9), 1185-1198 (15 pages).
Turkevich, John et al., "A study of the nucleation and growth processes in the synthesis of colloidal gold," Discuss. Faraday Soc., 1951,11, 55-75 (23 pages).
Zhu, Congzhi et al., "Mingling Electronic Chemical Sensors with Supramolecular Host-Guest Chemistry," Current Organic Chemistry, 2014, 18, 1957-1964 (8 pages).
Capuano, Rosamaria et al., "Corroles-Porphyrins: A Teamwork for Gas Sensor Arrays," Sensors, 2015, vol. 15, pp. 8121-8130 (10 pages).
Iezhokin, I. et al., "Porphyrin molecules boost the sensitivity of epitaxial graphene for NH3 detection," J. Phy.: Condens. Matter 29 (2017) (11 pages).
International Search Report and Written Opinion for PCT Application No. PCT/US2019/028870 dated Aug. 20, 2019 (17 pages).
Liu, Sophie F. et al., "Single-walled Carbon Nanotube-Metalloporphyrin Chemiresistive Gas Sensor Arrays for Volatile Organic Compounds," Chemistry of Materials, vol. 27, No. 10 (2015) pp. 3560-3563 (5 pages).
Rushi, A.D. et al., "Exercising Substituents in porphyrins for real time selective sensing of volatile organic compounds," Sensors and Actuators B: Chemical, vol. 257, 2018, pp. 389-397 (9 pages).
"International Search Report and Written Opinion," for PCT Application No. PCT/US2021/033872 dated Sep. 13, 2021 (14 pages).
"Office Action," for Japanese Patent Application No. 2020-566542 dated Aug. 24, 2021 (9 pages) with English Translation.
Meng, Zheng, et al. "Electrically-Transduced Chemical Sensors Based on Two-Dimensional Nanomaterials," Chem. Rev. 2019, 119, 478-598 (122 pages).
"Response to Communication Pursuant to Rules 161(1) and 162 EPC," for European Patent Application No. 19733177.0 filed Jun. 4, 2021 (20 pages).
"Response to Examination Report," for Australian Patent Application No. 2019224011 filed Jul. 23, 2021 (22 pages).
International Preliminary Report on Patentability for PCT Application No. PCT/US2019/018741 dated Sep. 3, 2020 (11 pages).
International Preliminary Report on Patentability for PCT Application No. PCT/US2019/028870 dated Nov. 5, 2020 (11 pages).
"First Examination Report," for Australian Patent Application No. 2019260666 dated Oct. 13, 2021 (4 pages).
"Office Action," for Japanese Patent Application No. 2020-558952 dated Dec. 7, 2021 (3 pages) No English Translation.
"Response to Examination Report," for Australian Patent Application No. 2019260666 filed Oct. 29, 2021 (20 pages).

\* cited by examiner

CHEMICAL SENSORS WITH NON-COVALENT, ELECTROSTATIC SURFACE MODIFICATION OF GRAPHENE

This application claims the benefit of U.S. Provisional Application No. 62/662,305, filed Apr. 25, 2018, the content of which is herein incorporated by reference in its entirety.

FIELD

Embodiments herein relate to chemical sensors, devices and systems including the same, and related methods. More specifically, embodiments herein relate to chemical sensors based on the non-covalent surface modification of graphene through electrostatic interactions.

BACKGROUND

The accurate detection of diseases can allow clinicians to provide appropriate therapeutic interventions. The early detection of diseases can lead to better treatment outcomes. Diseases can be detected using many different techniques including analyzing tissue samples, analyzing various bodily fluids, diagnostic scans, genetic sequencing, and the like.

Some disease states result in the production of specific chemical compounds. In some cases, volatile organic compounds (VOCs) released into a gaseous sample of a patient can be hallmarks of certain diseases. The detection of these compounds or differential sensing of the same can allow for the early detection of particular disease states.

SUMMARY

In a first aspect, a medical device is included. The medical device can include a graphene varactor. The graphene varactor can include a graphene layer and a self-assembled monolayer disposed on an outer surface of the graphene layer through electrostatic interactions between a partial positive charge on hydrogen atoms of one or more hydrocarbons of the self-assembled monolayer and a n-electron system of graphene. The self-assembled monolayer can include one or more substituted porphyrins or substituted metalloporphyrins, or derivatives thereof.

In a second aspect, in addition to one or more of the preceding or following aspects, or in the alternative to some aspects, the self-assembled monolayer can provide a Langmuir theta value of at least 0.9.

In a third aspect, in addition to one or more of the preceding or following aspects, or in the alternative to some aspects, the self-assembled monolayer can provide a Langmuir theta value of at least 0.98.

In a fourth aspect, in addition to one or more of the preceding or following aspects, or in the alternative to some aspects, the self-assembled monolayer can include substituted porphyrins of the formula:

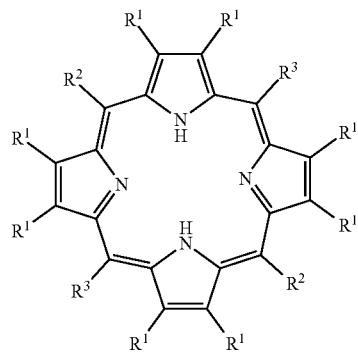

where each $R^1$ functional group can independently include: —H; —X, where X is a halogen atom; any linear or branched $C_1$-$C_{50}$ alkyl, $C_1$-$C_{50}$ alkenyl, $C_1$-$C_{50}$ alkynyl, $C_1$-$C_{50}$ heteroalkyl, $C_1$-$C_{50}$ heteroalkenyl, $C_1$-$C_{50}$ heteroalkynyl, or any combination thereof; —RZR, —ZRZR, or —RZRZR, where R can include, but not be limited to, any identical or different, linear or branched, $C_1$-$C_{50}$ alkyl, $C_1$-$C_{50}$ alkenyl, $C_1$-$C_{50}$ alkynyl, or any combination thereof, and Z can be one or more heteroatom selected from N, O, P, S, Se, or Si; —ROH, —RC(O)OH, —RC(O)OR, —ROR, —RSR, —RCHO, —RX, —RC(O)NH$_2$, —RC(O)NR, —RNH$_3^+$, —RNH$_2$, —RNO$_2$, —RNR, —RNRR, —RB(OH)$_2$, or any combination thereof, where R can include any identical or different, linear, branched, or cyclic $C_1$-$C_{50}$ alkyl, $C_1$-$C_{50}$ alkenyl, $C_1$-$C_{50}$ alkynyl, or a combination thereof, or can be absent such that the remaining portion of the functional group is covalently bound directly to one or more carbon atoms of the substituted porphyrin; and where each $R^2$ and $R^3$ functional group are independently: —H; any linear or branched $C_1$-$C_{50}$ alkyl, $C_1$-$C_{50}$ alkenyl, $C_1$-$C_{50}$ alkynyl, $C_1$-$C_{50}$ heteroalkyl, $C_1$-$C_{50}$ heteroalkenyl, $C_1$-$C_{50}$ heteroalkynyl or any combination thereof; —RZR or —RZRZR, where R can include any identical or different, linear or branched, $C_1$-$C_{50}$ alkyl, $C_1$-$C_{50}$ alkenyl, $C_1$-$C_{50}$ alkynyl, or any combination thereof, and Z can be one or more heteroatom selected from N, O, P, S, Se, or Si; an aryl, heteroaryl, substituted aryl, or substituted heteroaryl; a biphenyl or substituted biphenyl; an aryloxy, arylthio, arylamine, or any substitutions thereof; or any combination thereof; and where $R^1$, $R^2$, and $R^3$ are each covalently bound directly to the substituted porphyrin.

In a fifth aspect, in addition to one or more of the preceding or following aspects, or in the alternative to some aspects, the $R^2$ and $R^3$ functional groups are different than each other.

In a sixth aspect, in addition to one or more of the preceding or following aspects, or in the alternative to some aspects, each alkyl, alkenyl, alkynyl, heteroalkyl, heteroalkenyl, or heteroalkynyl functional group can independently include any linear or branched hydrocarbon functional group having from 6 to 32 carbon atoms ($C_6$-$C_{32}$).

In a seventh aspect, in addition to one or more of the preceding or following aspects, or in the alternative to some aspects, the self-assembled monolayer can include substituted porphyrins of the formula:

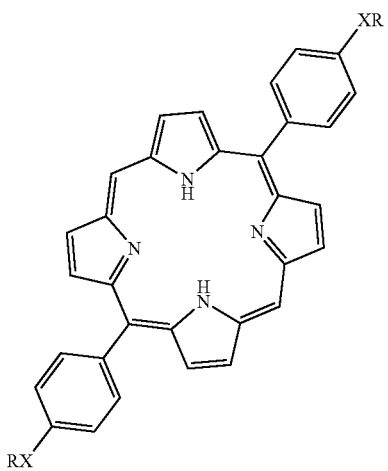

where each X is independently a heteroatom selected from N, O, P, S, Se, or Si, or absent, such that R is covalently attached to the phenyl group; and where each R functional group can independently include: —H; any linear or branched $C_1$-$C_{50}$ alkyl, $C_1$-$C_{50}$ alkenyl, $C_1$-$C_{50}$ alkynyl, $C_1$-$C_{50}$ heteroalkyl, $C_1$-$C_{50}$ heteroalkenyl, $C_1$-$C_{50}$ heteroalkynyl, or any combination thereof; —RZR, —ZRZR, or —RZRZR, where R can include any identical or different, linear or branched, $C_1$-$C_{50}$ alkyl, $C_1$-$C_{50}$ alkenyl, $C_1$-$C_{50}$ alkynyl, or any combination thereof, and Z can be one or more heteroatom selected from N, O, P, S, Se, or Si; an aryl, heteroaryl, substituted aryl, or substituted heteroaryl; a biphenyl or substituted biphenyl; an aryloxy, arylthio, arylamine, or any substitutions thereof; or any combination thereof.

In an eighth aspect, in addition to one or more of the preceding or following aspects, or in the alternative to some aspects, the self-assembled monolayer can include substituted porphyrins of the formula:

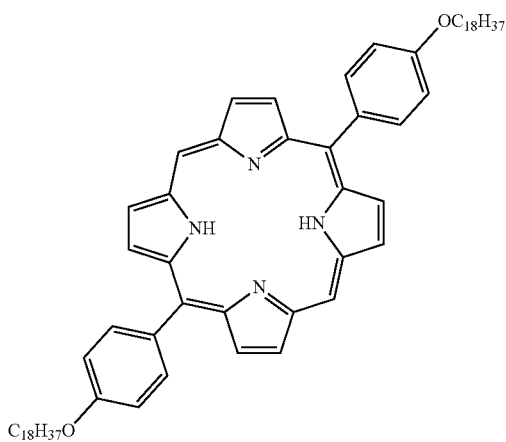

In a ninth aspect, in addition to one or more of the preceding or following aspects, or in the alternative to some aspects, the self-assembled monolayer can include substituted metalloporphyrins of the formula:

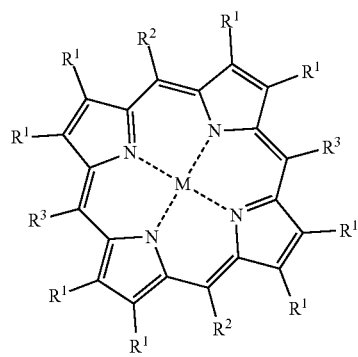

where each $R^1$ functional group can independently include —H; —X, where X is a halogen atom; any linear or branched $C_1$-$C_{50}$ alkyl, $C_1$-$C_{50}$ alkenyl, $C_1$-$C_{50}$ alkynyl, $C_1$-$C_{50}$ heteroalkyl, $C_1$-$C_{50}$ heteroalkenyl, $C_1$-$C_{50}$ heteroalkynyl, or any combination thereof; —RZR, —ZRZR, or —RZRZR, where R can include any identical or different, linear or branched, $C_1$-$C_{50}$ alkyl, $C_1$-$C_{50}$ alkenyl, $C_1$-$C_{50}$ alkynyl, or any combination thereof, and Z can be one or more heteroatom selected from N, O, P, S, Se, or Si; —ROH, —RC(O)OH, —RC(O)OR, —ROR, —RSR, —RCHO, —RX, —RC(O)NH$_2$, —RC(O)NR, —RNH$_3^+$, —RNH$_2$, —RNO$_2$, —RNR, —RNRR, —RB(OH)$_2$, or any combination thereof, where R can include any identical or different, linear, branched, or cyclic $C_1$-$C_{50}$ alkyl, $C_1$-$C_{50}$ alkenyl, $C_1$-$C_{50}$ alkynyl, or a combination thereof, or is absent such that the remaining portion of the functional group is covalently bound directly to one or more carbon atoms of the substituted metalloporphyrin; and where each $R^2$ and $R^3$ functional group can independently include: —H; any linear or branched $C_1$-$C_{50}$ alkyl, $C_1$-$C_{50}$ alkenyl, $C_1$-$C_{50}$ alkynyl, $C_1$-$C_{50}$ heteroalkyl, $C_1$-$C_{50}$ heteroalkenyl, $C_1$-$C_{50}$ heteroalkynyl, or any combination thereof; —RZR, —ZRZR, or —RZRZR, where R can include any identical or different, linear or branched, $C_1$-$C_{50}$ alkyl, $C_1$-$C_{50}$ alkenyl, $C_1$-$C_{50}$ alkynyl, or any combination thereof, and Z can be one or more heteroatom selected from N, O, P, S, Se, or Si; an aryl, heteroaryl, substituted aryl, or substituted heteroaryl; a biphenyl or substituted biphenyl; an aryloxy, arylthio, arylamine, or any substitutions thereof; or any combination thereof; and where $R^1$, $R^2$, and $R^3$ are each covalently bound directly to the substituted metalloporphyrin; and where M is a metal, including, but not limited to, aluminum, calcium, magnesium, manganese, iron, cobalt, nickel, zinc, ruthenium, palladium, silver, platinum, indium, tin, copper, rhodium, chromium, gallium, osmium, iridium, or derivatives thereof; and where an oxidation state of the metal can include, but not be limited to an oxidation state of I, II, III, IV, V, VI, VII, or VIII. Various inorganic, organic, ionic, or neutral ligands can be coordinated with the metals herein, including, but not to be limited to, Cl$^-$, F$^-$, Br$^-$, I$^-$, CN$^-$, SCN$^-$, CO, NH$_3$, H$_2$O, NO, CH$_3$NH$_2$, pyridine, and the like. The number of ligands can be from zero ligands to eight ligands.

In a tenth aspect, in addition to one or more of the preceding or following aspects, or in the alternative to some aspects, the self-assembled monolayer can include substituted metalloporphyrins of the formula:

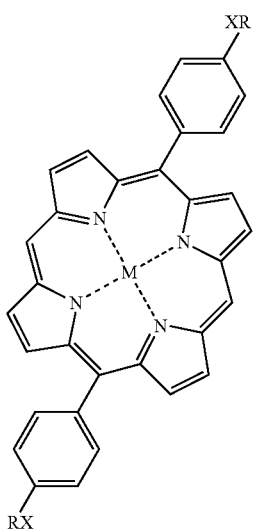

where each X is independently a heteroatom selected from N, O, P, S, Se, or Si, or absent, such that R is covalently attached to the phenyl group; and where each R functional group can independently include: —H; any linear or branched $C_1$-$C_{50}$ alkyl, $C_1$-$C_{50}$ alkenyl, $C_1$-$C_{50}$ alkynyl, $C_1$-$C_{50}$ heteroalkyl, $C_1$-$C_{50}$ heteroalkenyl, $C_1$-$C_{50}$ heteroalkynyl, or any combination thereof; —RZR, —ZRZR, or —RZRZR, where R can include any identical or different, linear or branched, $C_1$-$C_{50}$ alkyl, $C_1$-$C_{50}$ alkenyl, $C_1$-$C_{50}$ alkynyl, or any combination thereof, and Z can be one or more heteroatom selected from N, O, P, S, Se, or Si; an aryl, heteroaryl, substituted aryl, or substituted heteroaryl; a biphenyl or substituted biphenyl; an aryloxy, arylthio, arylamine, or any substitutions thereof; or any combination thereof; and where M is a metal including, but not limited to, aluminum, calcium, magnesium, manganese, iron, cobalt, nickel, zinc, ruthenium, palladium, silver, platinum, indium, tin, copper, rhodium, chromium, gallium, osmium, iridium, or derivatives thereof; and where an oxidation state of the metal include, but not be limited to an oxidation state of I, II, III, IV, V, VI, VII, or VIII. Various inorganic, organic, ionic, or neutral ligands can be coordinated with the metals herein, including, but not to be limited to, $Cl^-$, $F^-$, $Br^-$, $I^-$, $CN^-$, $SCN^-$, CO, $NH_3$, $H_2O$, NO, $CH_3NH_2$, pyridine, and the like. The number of ligands can be from zero ligands to eight ligands.

In an eleventh aspect, in addition to one or more of the preceding or following aspects, or in the alternative to some aspects, the self-assembled monolayer can provide coverage over the graphene from 50% to 150% by surface area.

In a twelfth aspect, in addition to one or more of the preceding or following aspects, or in the alternative to some aspects, the self-assembled monolayer can provide coverage over the graphene from 99% to 120% by surface area.

In a thirteenth aspect, in addition to one or more of the preceding or following aspects, or in the alternative to some aspects, a method of modifying a surface of graphene to create a graphene varactor is included. The method can include forming a self-assembled monolayer disposed on an outer surface of a graphene layer through electrostatic interactions between a partial positive charge on hydrogen atoms of one or more hydrocarbons of the self-assembled monolayer and a π-electron system of graphene. The self-assembled monolayer of the method can include one or more substituted porphyrins or substituted metalloporphyrins. The method can include quantifying the extent of surface coverage of the self-assembled monolayer using contact angle goniometry, Raman spectroscopy, or X-Ray photoelectron spectroscopy.

In a fourteenth aspect, in addition to one or more of the preceding or following aspects, or in the alternative to some aspects, the step of selecting derivatized graphene layers can include selecting derivatized graphene layers that exhibit a Langmuir theta value of at least 0.9.

In a fifteenth aspect, in addition to one or more of the preceding or following aspects, or in the alternative to some aspects, the step of selecting derivatized graphene layers can include selecting derivatized graphene layers that exhibit a Langmuir theta value of at least 0.98.

In a sixteenth aspect, in addition to one or more of the preceding or following aspects, or in the alternative to some aspects, a method for detecting an analyte is included. The method can include collecting a gaseous sample from a patient. The method can include contacting a graphene reactor, as described herein.

In a seventeenth aspect, in addition to one or more of the preceding or following aspects, or in the alternative to some aspects, the medical device can include a plurality of graphene varactors configured in an array on the medical device.

In an eighteenth aspect, in addition to one or more of the preceding or following aspects, or in the alternative to some aspects, a method for detecting an analyte is included. The method can include collecting a gaseous sample from a patient and contacting the gaseous sample with one or more graphene varactors. Each of the one or more graphene varactors can include a graphene layer and a self-assembled monolayer disposed on an outer surface of the graphene layer through electrostatic interactions between a partial positive charge on hydrogen atoms of one or more hydrocarbons of the self-assembled monolayer and a π-electron system of graphene. The self-assembled monolayer can include at least one selected from substituted porphyrins or substituted metalloporphyrins, or derivatives thereof, as described herein.

In a nineteenth aspect, in addition to one or more of the preceding or following aspects, or in the alternative to some aspects, the method can include measuring a differential response in an electrical property of the one or more graphene varactors due to the binding of one or more analytes present in the gaseous sample.

In a twentieth aspect, in addition to one or more of the preceding or following aspects, or in the alternative to some aspects, the method can include the step of measuring an electrical property selected from the group including capacitance or resistance.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

Figure 1:
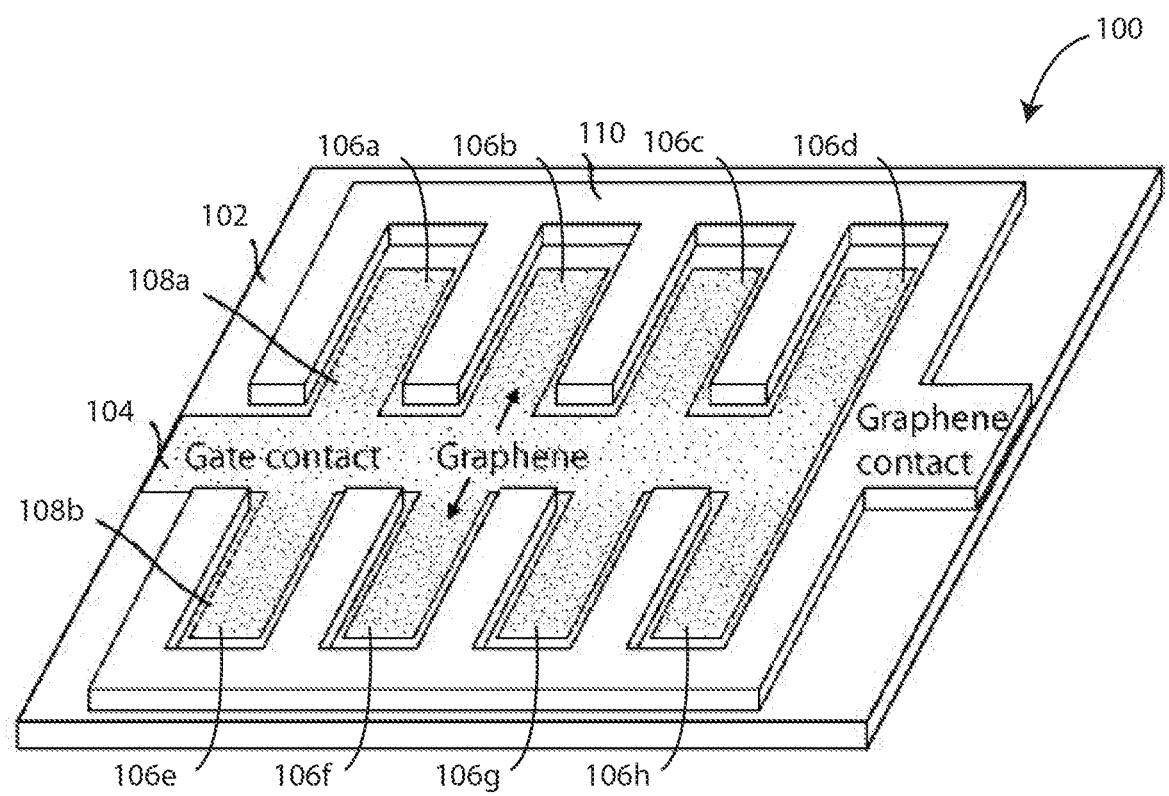
FIG. 1 is a schematic perspective view of a graphene varactor in accordance with various embodiments herein.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

Embodiments herein relate to chemical sensors, medical devices and systems including the same, and related methods for detecting chemical compounds in gaseous samples, such as, but not limited to, the breath of a patient. In some embodiments, the chemical sensors herein can be based on the non-covalent surface modification of graphene with substituted porphyrins or substituted metalloporphyrins.

Graphene is a form of carbon containing a single layer of carbon atoms in a hexagonal lattice. Graphene has a high strength and stability due to its tightly packed sp² hybridized orbitals, where each carbon atom forms one sigma (G) bond each with its three neighboring carbon atoms and has one p orbital projected out of the hexagonal plane. The p orbitals of the hexagonal lattice can hybridize to form a π band on the surface of graphene that is suitable for non-covalent electrostatic interaction and π-π stacking interactions with other molecules.

Porphyrins are a group of heterocyclic macrocycles having four modified pyrrole subunits, each connected by a methine (=CH—) bridge. The basic core structure of an unsubstituted porphyrin is called porphine, which has 18 π-electrons that creates a continuous aromatic cycle about the molecule. The structure of porphine, showing its 18 π-electron cycle in bold, is as follows:

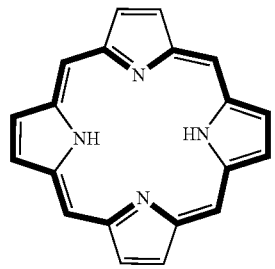

Porphyrins can further exist complexed with a metal ion or derivative thereof to form a metalloporphyrin.

Porphyrins or metalloporphyrins substituted, for example, with one or more alkyl groups can form a well-ordered, non-covalently bound monolayer on the surface of graphene, where the density of substituted porphyrins or substituted metalloporphyrins is maximized, and the substituted porphyrins or substituted metalloporphyrins are adsorbed onto the surface of the graphene in highly ordered pattern similar to a two-dimensional crystal.

Without wishing to be bound by any particular theory, it is believed that hydrogen atoms within hydrocarbon groups (e.g., alkyl chains) can interact with the π electron system on the surface of graphene through electrostatic interactions. Hydrogen atoms have low electronegativity, and as such, they carry a partial positive charge. The partial positive charge on the hydrogen atoms of alkyl chains can participate in electrostatic interactions with the π electron system of the π band on the surface of graphene. The alkyl chains can adsorb onto the graphene surface in an all trans conformation along the carbon-carbon backbone, such that all carbon atoms fall into one plane that is either perpendicular or parallel to the graphene surface.

By way of example, the trans conformation of an alkyl chain having a perpendicular orientation of its carbon-carbon backbone along the surface of graphene creates a configuration where every second —CH₂— group of the alkyl chain has its hydrogen atoms pointing towards the graphene. As such, alkyl chains can orient themselves with respect to the graphene surface so that the —CH₂— hydrogens of alternate —CH₂— groups are disposed the same distance from the graphene surface and the hydrogen-graphene interactions are maximized. Thus, the alkyl chain can interact with the surface of graphene along the length of the alkyl chain. It is also believed that the hydrogen atoms of alkenyl chains and alkynyl chains, and derivatives thereof, can similarly interact with the graphene surface.

The non-covalent functionalization of graphene with a self-assembled monolayer of porphyrins or metalloporphyrins substituted with, for example, hydrocarbon groups, does not significantly affect the atomic structure of graphene, and provides a stable graphene-based sensor with high sensitivity towards a number of volatile organic compounds (VOCs) in the parts-per-billion (ppb) or parts-per-million (ppm) levels. As such, the embodiments herein can be used to detect VOCs and/or differential binding patterns of the same that, in turn, can be used to identify disease states.

Referring now to FIG. 1, a schematic view of a graphene-based variable capacitor (or graphene varactor) 100 is shown in accordance with the embodiments herein. It will be appreciated that graphene varactors can be prepared in various ways with various geometries, and that the graphene varactor shown in FIG. 1 is just one example in accordance with the embodiments herein.

Graphene varactor 100 can include an insulator layer 102, a gate electrode 104 (or "gate contact"), a dielectric layer (not shown in FIG. 1), one or more graphene layers, such as graphene layers 108a and 108b, and a contact electrode 110 (or "graphene contact"). In some embodiments, the graphene layer(s) 108a-b can be contiguous, while in other embodiments the graphene layer(s) 108a-b can be non-contiguous. Gate electrode 104 can be deposited within one or more depressions formed in insulator layer 102. Insulator layer 102 can be formed from an insulative material such as silicon dioxide, formed on a silicon substrate (wafer), and the like. Gate electrode 104 can be formed by an electrically conductive material such as chromium, copper, gold, silver, nickel, tungsten, aluminum, titanium, palladium, platinum, iridium, and any combinations or alloys thereof, which can be deposited on top of or embedded within the insulator layer 102. The dielectric layer can be disposed on a surface of the insulator layer 102 and the gate electrode 104. The graphene layer(s) 108a-b can be disposed on the dielectric layer. The dielectric layer will be discussed in more detail below in reference to FIG. 2.

Graphene varactor 100 includes eight gate electrode fingers 106a-106h. It will be appreciated that while graphene varactor 100 shows eight gate electrode fingers 106a-106h, any number of gate electrode finger configurations can be contemplated. In some embodiments, an individual graphene varactor can include fewer than eight gate electrode fingers. In some embodiments, an individual graphene varactor can include more than eight gate electrode fingers. In other embodiments, an individual graphene varactor can include two gate electrode fingers. In some embodiments, an individual graphene varactor can include 1, 2, 3, 4, 5, 6, 7, 8, 9, 10, or more gate electrode fingers.

Graphene varactor 100 can include one or more contact electrodes 110 disposed on portions of the graphene layers 108a and 108b. Contact electrode 110 can be formed from an electrically conductive material such as chromium, copper, gold, silver, nickel, tungsten, aluminum, titanium, palladium, platinum, iridium, and any combinations or alloys thereof. Further aspects of exemplary graphene varactors can be found in U.S. Pat. No. 9,513,244, the content of which is herein incorporated by reference in its entirety.

The graphene varactors described herein can include those in which a single graphene layer has been surface-modified through non-covalent electrostatic interactions between graphene and molecules substituted with hydrocarbon groups. In some embodiments, the surface of a single graphene layer can be surface-modified through non-covalent electrostatic interactions between graphene and any one of a number of substituted porphyrins or derivatives thereof. In some embodiments, the surface of a single graphene layer can be surface-modified through non-covalent electrostatic interactions between graphene and any one of a number of substituted metalloporphyrins derivatives thereof. Details regarding the graphene varactors and substituted porphyrins or substituted metalloporphyrins suitable for use herein will be discussed more fully below.

Figure 2:
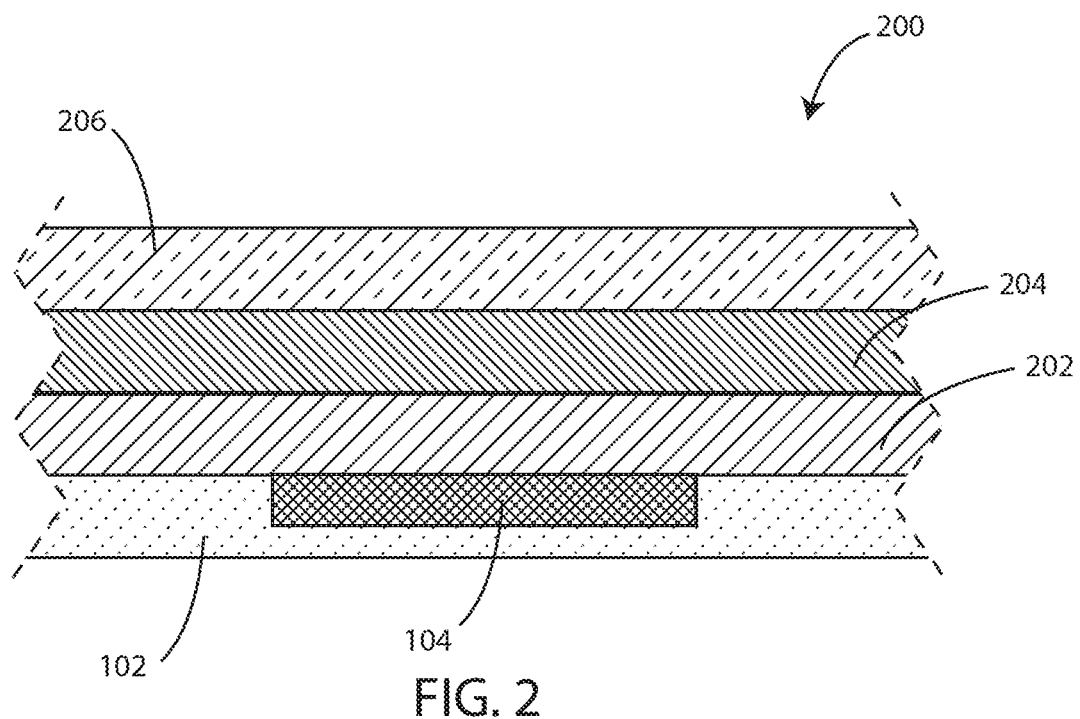
FIG. 2 is a schematic cross-sectional view of a portion of a graphene varactor in accordance with various embodiments herein.

Referring now to FIG. 2, a schematic cross-sectional view of a portion of a graphene varactor 200 is shown in accordance with various embodiments herein. The graphene varactor 200 can include an insulator layer 102 and a gate electrode 104 recessed into the insulator layer 102. The gate electrode 104 can be formed by depositing an electrically conductive material in the depression in the insulator layer 102, as discussed above in reference to FIG. 1. A dielectric layer 202 can be formed on a surface of the insulator layer 102 and the gate electrode 104. In some examples, the dielectric layer 202 can be formed of a material, such as, silicon dioxide, aluminum oxide, hafnium dioxide, zirconium dioxide, hafnium silicate, or zirconium silicate.

The graphene varactor 200 can include a single graphene layer 204 that can be disposed on a surface of the dielectric layer 202. The graphene layer 204 can be surface-modified with a self-assembled monolayer 206. The self-assembled monolayer 206 can be formed of a homogenous population of substituted porphyrins or substituted metalloporphyrins disposed on an outer surface of the graphene layer 204 through non-covalent electrostatic interactions. Exemplary substituted porphyrins or substituted metalloporphyrins are described more fully below. The self-assembled monolayer 206 can provide at least 90% surface coverage (by area) of the graphene layer 204. In some embodiments, the self-assembled monolayer 206 can provide at least 95% surface coverage of the graphene layer 204. In other embodiments, the self-assembled monolayer 206 can provide at least 98% surface coverage of the graphene layer 204.

In some embodiments, the self-assembled monolayer can provide at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99%, or 100% surface coverage (by area) of the graphene layer. It will be appreciated that the self-assembled monolayer can provide surface coverage falling within a range wherein any of the forgoing percentages can serve as the lower or upper bound of the range, provided that the lower bound of the range is a value less than the upper bound of the range.

In some embodiments, it will be appreciated that the self-assembly of substituted porphyrins or substituted metalloporphyrins on the surface of the graphene layer can include the self-assembly into more than a monolayer, such as a multilayer. Multilayers can be detected and quantified by techniques such as scanning tunneling microscopy (STM) and other scanning probe microscopies. References herein to a percentage of coverage greater than 100% shall refer to the circumstance where a portion of the surface area is covered by more than a monolayer, such as covered by two, three or potentially more layers of the compound used. Thus, a reference to 105% coverage herein shall indicate that approximately 5% of the surface area includes more than monolayer coverage over the graphene layer. In some embodiments, graphene surfaces can include 101%, 102%, 103%, 104%, 105%, 110%, 120%, 130%, 140%, 150%, or 175% surface coverage of the graphene layer. It will be appreciated that multilayer surface coverage of the graphene layer can fall within a range of surface coverages, wherein any of the forgoing percentages can serve as the lower or upper bound of the range, provided that the lower bound of the range is a value less than the upper bound of the range. For example, ranges of coverage can include, but are not limited to, 50% to 150% by surface area, 80% to 120% by surface area, 90% to 110%, or 99% to 120% by surface area.

In some embodiments, the self-assembled monolayers suitable for use herein can provide coverage of the graphene surface with a monolayer as quantified by the Langmuir theta value of at least some minimum threshold value, but avoid covering the majority of the surface of the graphene with a multilayer thicker than a monolayer. Details about the Langmuir theta values and determination of thereof for a particular self-assembled monolayer using Langmuir adsorption theory is described more fully below. In some embodiments, the self-assembled monolayers suitable for use herein provide a Langmuir theta value of at least 0.95. In some embodiments, the self-assembled monolayers suitable for use herein provide a Langmuir theta value of at least 0.98. In some embodiments, the self-assembled monolayers can provide a Langmuir theta value of at least 0.85, 0.86, 0.87, 0.88, 0.89, 0.90, 0.91, 0.92, 0.93, 0.94, 0.95, 0.96, 0.97, 0.98, 0.99, or 1.0. It will be appreciated that the self-assembled monolayer can provide a range of Langmuir theta values, wherein any of the forgoing Langmuir theta values can serve as the lower or upper bound of the range, provided that the lower bound of the range is a value less than the upper bound of the range.

Figure 3:
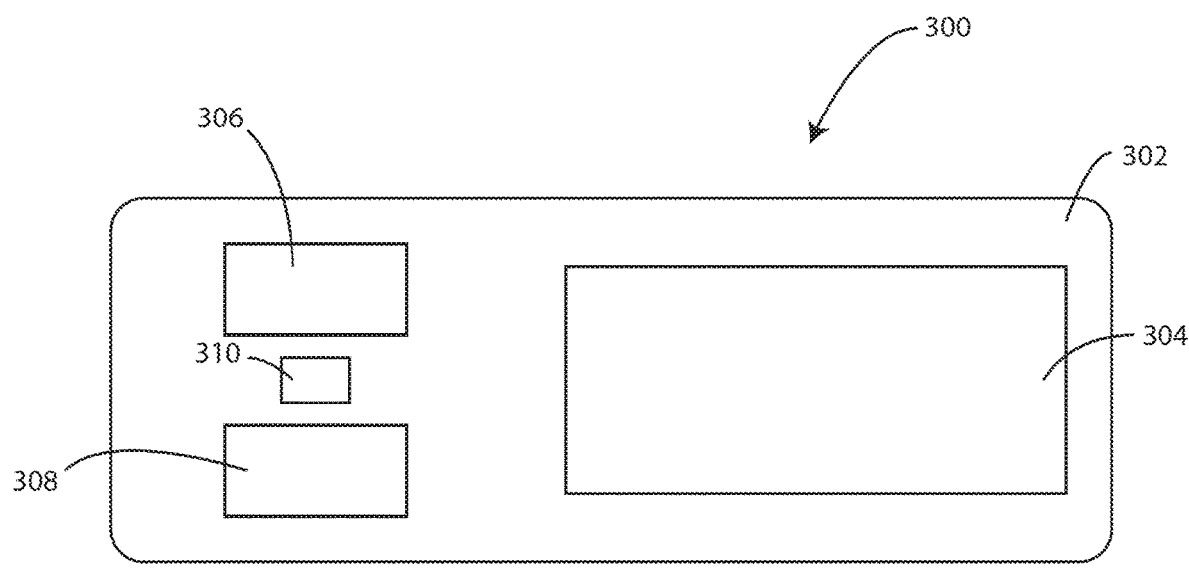
FIG. 3 is a schematic top plan view of a chemical sensor element in accordance with various embodiments herein.

Referring now to FIG. 3, a schematic top plan view of a chemical sensor element 300 is shown in accordance with various embodiments herein. The chemical sensor element 300 can include a substrate 302. It will be appreciated that the substrate can be formed from many different materials. By way of example, the substrate can be formed from silicon, glass, quartz, sapphire, polymers, metals, glasses, ceramics, cellulosic materials, composites, metal oxides, and the like. The thickness of the substrate can vary. In some embodiments, the substrate has sufficient structural integrity to be handled without undue flexure that could damage components thereon. In some embodiments, the substrate can have a thickness of about 0.05 mm to about 5 mm. The length and width of the substrate can also vary. In some embodiments, the length (or major axis) can be from about 0.2 cm to about 10 cm. In some embodiments, the length (or major axis) can be from about 20 µm to about 1 cm. In some embodiments, the width (perpendicular to the major axis) can be from about 0.2 cm to about 8 cm. In some embodiments, the width (perpendicular to the major axis) can be from about 20 µm to about 0.8 cm. In some embodiments, the graphene-based chemical sensor can be disposable.

A first measurement zone 304 can be disposed on the substrate 302. In some embodiments, the first measurement zone 304 can define a portion of a first gas flow path. The first measurement zone (or gas sample zone) 304 can include a plurality of discrete graphene-based variable capacitors (or graphene varactors) that can sense analytes in a gaseous sample, such as a breath sample. A second measurement zone (or environment sample zone) 306, separate from the first measurement zone 304, can also be disposed on the substrate 302. The second measurement zone 306 can also include a plurality of discrete graphene varactors. In some embodiments, the second measurement zone 306 can include the same (in type and/or number) discrete graphene varactors that are within the first measurement zone 304. In some embodiments, the second measurement zone 306 can include only a subset of the discrete graphene varactors that are within the first measurement zone 304. In operation, the data gathered from the first measurement zone, which can be reflective of the gaseous sample analyzed, can be corrected or normalized based on the data gathered from the second measurement zone, which can be reflective of analytes present in the environment.

In some embodiments, a third measurement zone (drift control or witness zone) 308 can also be disposed on the substrate. The third measurement zone 308 can include a plurality of discrete graphene varactors. In some embodiments, the third measurement zone 308 can include the same (in type and/or number) discrete graphene varactors that are within the first measurement zone 304. In some embodiments, the third measurement zone 308 can include only a subset of the discrete graphene varactors that are within the first measurement zone 304. In some embodiments, the third measurement zone 308 can include discrete graphene varactors that are different than those of the first measurement zone 304 and the second measurement zone 306. Aspects of the third measurement zone are described in greater detail below.

The first measurement zone, the second measurement zone, and the third measurement zone can be the same size or can be of different sizes. The chemical sensor element 300 can also include a component 310 to store reference data. The component 310 to store reference data can be an electronic data storage device, an optical data storage device, a printed data storage device (such as a printed code), or the like. The reference data can include, but is not limited to, data regarding the third measurement zone (described in greater detail below).

In some embodiments, chemical sensor elements embodied herein can include electrical contacts (not shown) that can be used to provide power to components on the chemical sensor element 300 and/or can be used to read data regarding the measurement zones and/or data from the stored in component 310. However, in other embodiments there are no external electrical contacts on the chemical sensor element 300.

Figure 5:
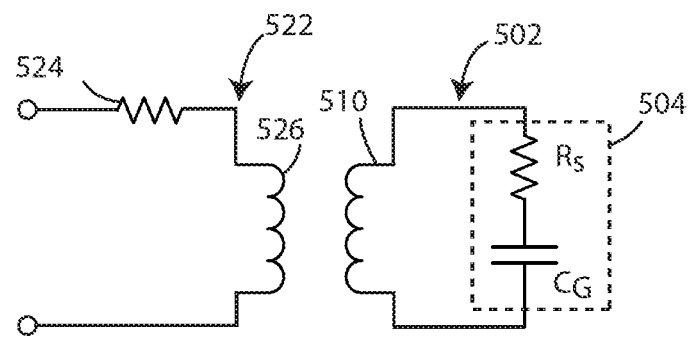
FIG. 5 is a circuit diagram of a passive sensor circuit and a portion of a reading circuit in accordance with various embodiments herein.

It will be appreciated that the chemical sensor elements embodied herein can include those that are compatible with passive wireless sensing. A schematic diagram of a passive sensor circuit 502 and a portion of a reading circuit 522 is shown in FIG. 5 and discussed in more detail below. In the passive wireless sensing arrangement, the graphene varactor(s) can be integrated with an inductor such that one terminal of the graphene varactor contacts one end of the inductor, and a second terminal of the graphene varactor contacts a second terminal of the inductor. In some embodiments, the inductor can be located on the same substrate as the graphene varactor, while in other embodiments, the inductor could be located in an off-chip location.

Figure 4:
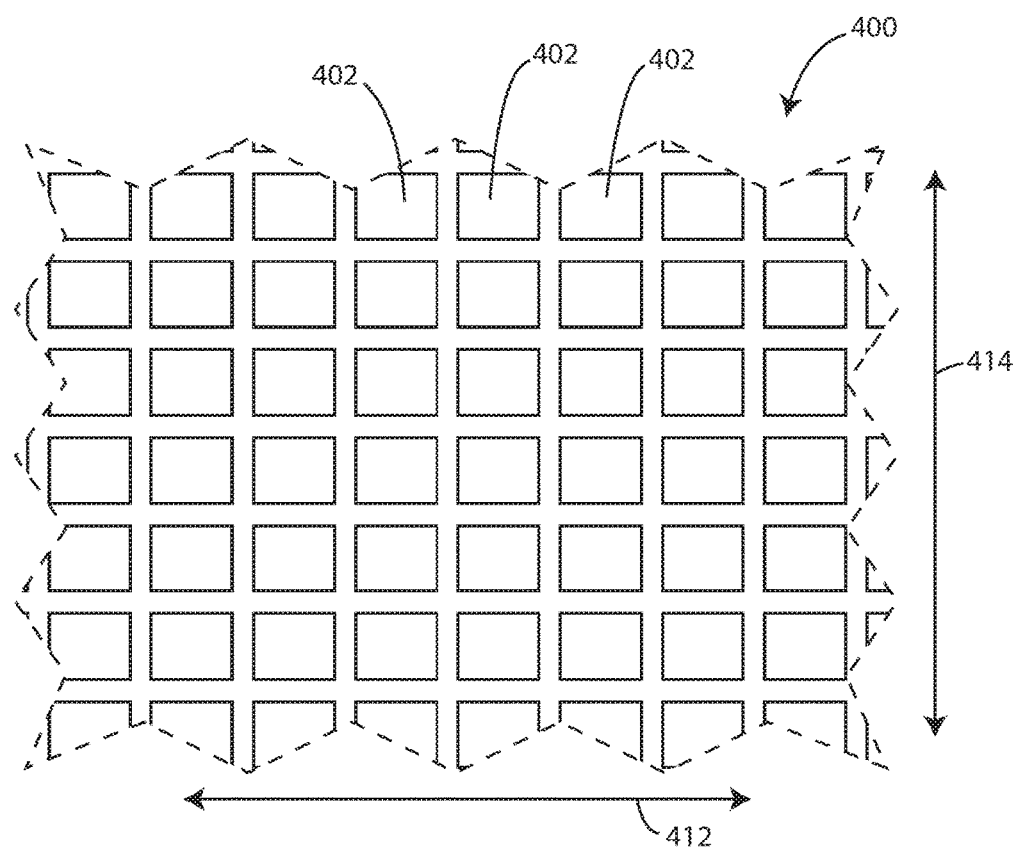
FIG. 4 is a schematic diagram of a portion of a measurement zone in accordance with various embodiments herein.

Referring now to FIG. 4, a schematic diagram of a portion of a measurement zone 400 is shown in accordance with various embodiments herein. A plurality of discrete graphene varactors 402 can be disposed within the measurement zone 400 in an array. In some embodiments, a chemical sensor element can include a plurality of graphene varactors configured in an array within a measurement zone. In some embodiments, the plurality of graphene varactors can be identical, while in other embodiments the plurality of graphene varactors can be different from one another.

In some embodiments, the discrete graphene varactors can be heterogeneous in that they are all different from one another in terms of their binding behavior specificity with regard to a particular analyte. In some embodiments, some discrete graphene varactors can be duplicated for validation purposes, but are otherwise heterogeneous from other discrete graphene varactors. Yet in other embodiments, the discrete graphene varactors can be homogeneous. While the discrete graphene varactors 402 of FIG. 4 are shown as boxes organized into a grid, it will be appreciated that the discrete graphene varactors can take on many different shapes (including, but not limited to, various polygons, circles, ovals, irregular shapes, and the like) and, in turn, the groups of discrete graphene varactors can be arranged into many different patterns (including, but not limited to, star patterns, zig-zag patterns, radial patterns, symbolic patterns, and the like).

In some embodiments, the order of specific discrete graphene varactors 402 across the length 412 and width 414 of the measurement zone can be substantially random. In other embodiments, the order can be specific. For example, in some embodiments, a measurement zone can be ordered so that the specific discrete graphene varactors 402 for analytes having a lower molecular weight are located farther away from the incoming gas flow relative to specific discrete graphene varactors 402 for analytes having a higher molecular weight which are located closer to the incoming gas flow. As such, chromatographic effects which may serve to provide separation between chemical compounds of different molecular weight can be taken advantage of to provide for optimal binding of chemical compounds to corresponding discrete graphene varactors.

The number of discrete graphene varactors within a particular measurement zone can be from about 1 to about 100,000. In some embodiments, the number of discrete graphene varactors can be from about 1 to about 10,000. In some embodiments, the number of discrete graphene varactors can be from about 1 to about 1,000. In some embodiments, the number of discrete graphene varactors can be from about 2 to about 500. In some embodiments, the number of discrete graphene varactors can be from about 10 to about 500. In some embodiments, the number of discrete graphene varactors can be from about 50 to about 500. In some embodiments, the number of discrete graphene varactors can be from about 1 to about 250. In some embodiments, the number of discrete graphene varactors can be from about 1 to about 50.

Each of the discrete graphene varactors suitable for use herein can include at least a portion of one or more electrical circuits. By way of example, in some embodiments, each of the discrete graphene varactors can include one or more passive electrical circuits. In some embodiments, the graphene varactors can be included such that they are integrated directly on an electronic circuit. In some embodiments, the graphene varactors can be included such that they are wafer bonded to the circuit. In some embodiments, the graphene varactors can include integrated readout electronics, such as a readout integrated circuit (ROIC). The electrical properties of the electrical circuit, including resistance or capacitance, can change upon binding, such as specific and/or nonspecific binding, with a component from a gas sample.

Referring now to FIG. 5, a schematic diagram of a passive sensor circuit 502 and a portion of a reading circuit 522 is shown in accordance with various aspects herein. In some embodiments, the passive sensor circuit 502 can include a metal-oxide-graphene varactor 504 (wherein RS represents the series resistance and CG represents the varactor capacitor) coupled to an inductor 510. Graphene varactors can be prepared in various ways and with various geometries. By way of example, in some aspects, a gate electrode can be recessed into an insulator layer as shown as gate electrode 104 in FIG. 1. A gate electrode can be formed by etching a depression into the insulator layer and then depositing an electrically conductive material in the depression to form the gate electrode. A dielectric layer can be formed on a surface of the insulator layer and the gate electrode. In some examples, the dielectric layer can be formed of a metal oxide such as, aluminum oxide, hafnium dioxide, zirconium dioxide, silicon dioxide, or of another material such as hafnium silicate or zirconium silicate. A surface-modified graphene layer can be disposed on the dielectric layer. Contact electrodes can also be disposed on a surface of the surface-modified graphene layer, also shown in FIG. 1 as contact electrode 110.

Further aspects of exemplary graphene varactor construction can be found in U.S. Pat. No. 9,513,244, the content of which is herein incorporated by reference in its entirety.

In various embodiments, the functionalized graphene layer (e.g., functionalized to include analyte binding receptors), which is part of the graphene varactor and thus part of a sensor circuit, such as a passive sensor circuit, is exposed to the gas sample flowing over the surface of the measurement zone. The passive sensor circuit 502 can also include an inductor 510. In some embodiments, only a single varactor is included with each passive sensor circuit 502. In other embodiments, multiple varactors are included, such as in parallel, with each passive sensor circuit 502.

In the passive sensor circuit 502, the capacitance of the electrical circuit changes upon binding of an analyte in the gas sample and the graphene varactor. The passive sensor circuit 502 can function as an LRC resonator circuit, wherein the resonant frequency of the LRC resonator circuit changes upon binding with a component from a gas sample.

The reading circuit 522 can be used to detect the electrical properties of the passive sensor circuit 502. By way of example, the reading circuit 522 can be used to detect the resonant frequency of the LRC resonator circuit and/or changes in the same. In some embodiments, the reading circuit 522 can include a reading coil having a resistance 524 and an inductance 526. When the sensor-side LRC circuit is at its resonant frequency, a plot of the phase of the impedance of the reading circuit versus the frequency has a minimum (or phase dip frequency). Sensing can occur when the varactor capacitance varies in response to binding of analytes, which changes the resonant frequency, and/or the value of the phase dip frequency.

Figure 6:
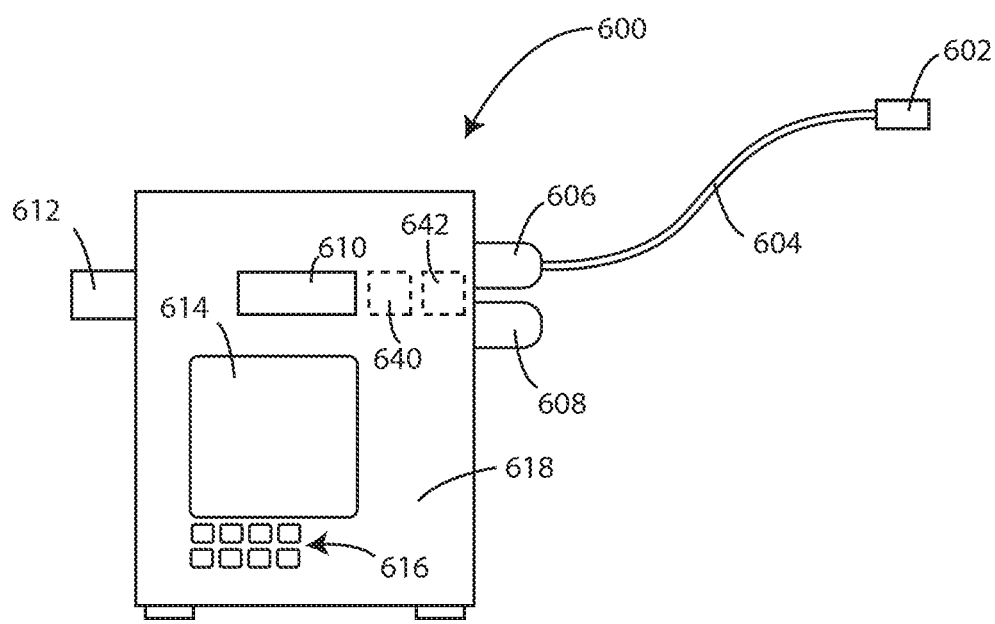
FIG. 6 is a schematic view of a system for sensing gaseous analytes in accordance with various embodiments herein.

Referring now to FIG. 6, a schematic view of a system 600 for sensing gaseous analytes in accordance with various embodiments herein is shown. The system 600 can include a housing 618. The system 600 can include a mouthpiece 602 into which a subject to be evaluated can blow a breath sample. The gaseous breath sample can pass through an inflow conduit 604 and pass through an evaluation sample (patient sample) input port 606. The system 600 can also include a control sample (environment) input port 608. The system 600 can also include a sensor element chamber 610, into which disposable sensor elements can be placed. The system 600 can also include a display screen 614 and a user input device 616, such as a keyboard. The system can also include a gas outflow port 612. The system 600 can also include flow sensors in fluid communication with the gas flow associated with one or more of the evaluation sample input port 606 and control sample input port 608. It will be appreciated that many different types of flow sensors can be used. In some embodiments, a hot-wire anemometer can be used to measure the flow of air. In some embodiments, the system can include a $CO_2$ sensor in fluid communication with the gas flow associated with one or more of the evaluation sample input port 606 and control sample input port 608.

In various embodiments, the system 600 can also include other functional components. By way of example, the system 600 can include a humidity control module 640 and/or a temperature control module 642. The humidity control module can be in fluid communication with the gas flow associated with one or more of the evaluation sample input port 606 and control sample input port 608 in order to adjust the humidity of one or both gas flow streams in order to make the relative humidity of the two streams substantially the same in order to prevent an adverse impact on the readings obtained by the system. The temperature control module can be in fluid communication with the gas flow associated with one or more of the evaluation sample input port 606 and control sample input port 608 in order to adjust the temperature of one or both gas flow streams in order to make the temperature of the two streams substantially the same in order to prevent an adverse impact on the readings obtained by the system. By way of example, the air flowing into the control sample input port can be brought up to 37 degrees Celsius or higher in order to match or exceed the temperature of air coming from a patient. The humidity control module and the temperature control module can be upstream from the input ports, within the input ports, or downstream from the input ports in the housing 618 of the system 600. In some embodiments, the humidity control module 640 and the temperature control module 642 can be integrated.

In some embodiments (not shown), the control sample input port 608 of system 600 can also be connected to a mouthpiece 602. In some embodiments, the mouthpiece 602 can include a switching airflow valve such that when the patient is drawing in breath, air flows from the control sample input port 608 to the mouthpiece, and the system is configured so that this causes ambient air to flow across the appropriate control measurement zone (such as the second measurement zone). Then when the patient exhales, the switching airflow valve can switch so that a breath sample from the patient flows from the mouthpiece 602 through the inflow conduit 604 and into the evaluation sample input port 606 and across the appropriate sample (patient sample) measurement zone (such as the first measurement zone) on the disposable sensor element.

In an embodiment, a method of making a chemical sensor element is included. The method can include depositing one or more measurement zones onto a substrate. The method can further include depositing a plurality of discrete graphene varactors within the measurement zones on the substrate. The method can include generating one or more discrete graphene varactors by modifying a surface of a graphene layer with substituted porphyrins or substituted metalloporphyrins to form a self-assembled monolayer on an outer surface of the graphene layer through electrostatic interactions. The method can include quantifying the extent of surface coverage of the self-assembled monolayer using contact angle goniometry, Raman spectroscopy, or X-Ray photoelectron spectroscopy. The method can include selecting derivatized graphene layers that exhibit a Langmuir theta value of at least 0.9, as will be discussed more fully below. In some embodiments, the method can include selecting derivatized graphene layers that exhibit a Langmuir theta value of at least 0.98. The method can further include depositing a component to store reference data onto the substrate. In some embodiments, the measurement zones can all be placed on the same side of the substrate. In other embodiments, the measurement zones can be placed onto different sides of the substrate.

In an embodiment, a method of assaying one or more gas samples is included. The method can include inserting a chemical sensor element into a sensing machine. The chemical sensor element can include a substrate and a first measurement zone comprising a plurality of discrete graphene varactors. The first measurement zone can define a portion of a first gas flow path. The chemical sensor element can further include a second measurement zone separate from the first measurement zone. The second measurement zone can also include a plurality of discrete graphene varactors. The second measurement zone can be disposed outside of the first gas flow path.

The method can further include prompting a subject to blow air into the sensing machine to follow the first gas flow path. In some embodiments, the $CO_2$ content of the air from the subject is monitored and sampling with the disposable sensor element is conducted during the plateau of $CO_2$ content, as it is believed that the air originating from the alveoli of the patient has the richest content of chemical compounds for analysis, such as volatile organic compounds. In some embodiments, the method can include monitoring the total mass flow of the breath sample and the control (or environmental) air sample using flow sensors. The method can further include interrogating the discrete graphene varactors to determine their analyte binding status. The method can further include discarding the disposable sensor element upon completion of sampling.

Figure 7:
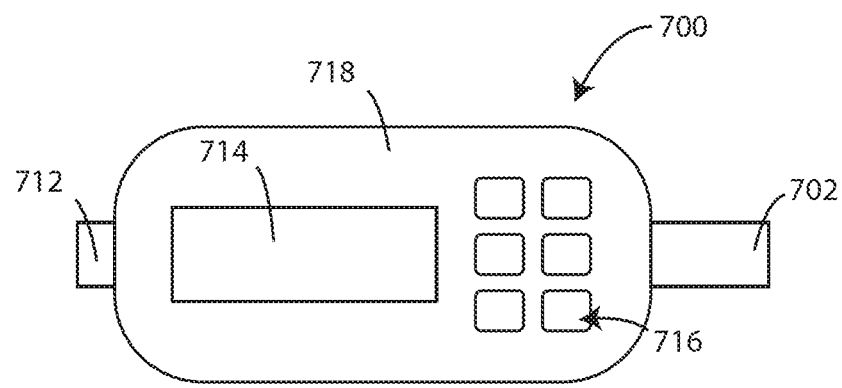
FIG. 7 is a schematic view of a system for sensing gaseous analytes in accordance with various embodiments herein.

Referring now to FIG. 7, a schematic view of a system 700 for sensing gaseous analytes in accordance with various embodiments herein is shown. In this embodiment, the system is in a hand-held format. The system 700 can include a housing 718. The system 700 can include a mouthpiece 702 into which a subject to be evaluated can blow a breath sample. The system 700 can also include a display screen 714 and a user input device 716, such as a keyboard. The system can also include a gas outflow port 712. The system can also include various other components such as those described with reference to FIG. 6 above.

In some embodiments, one of the measurement zones can be configured to indicate changes (or drift) in the chemical sensor element that could occur as a result of aging and exposure to varying conditions (such as heat exposure, light exposure, molecular oxygen exposure, humidity exposure, etc.) during storage and handling prior to use. In some embodiments, the third measurement zone can be configured for this purpose.

Figure 8:
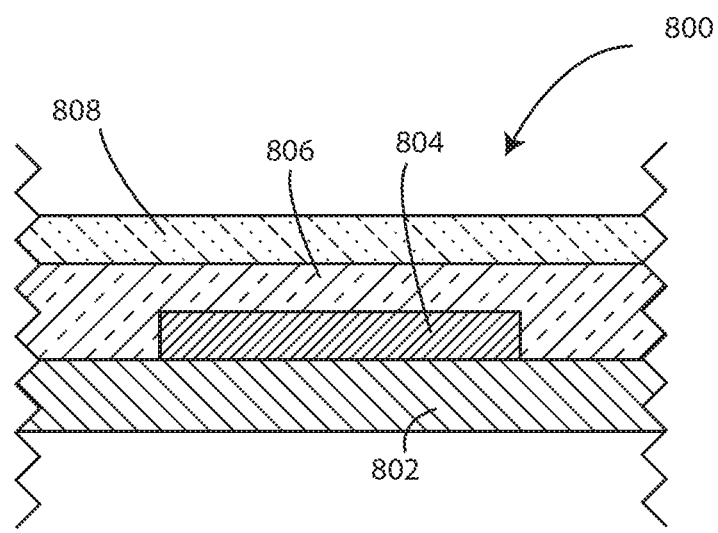
FIG. 8 is a schematic cross-sectional view of a portion of a chemical sensor element in accordance with various embodiments herein.

Referring now to FIG. 8, a schematic cross-sectional view is shown of a portion of a chemical sensor element 800 in accordance with various embodiments herein. The chemical sensor element 800 can include a substrate 802 and a discrete graphene varactor 804 disposed thereon that is part of a measurement zone. Optionally, in some embodiments the discrete graphene varactor 804 can be encapsulated by an inert material 806, such as nitrogen gas, or an inert liquid or solid. In this manner, the discrete graphene varactor 804 for the third measurement zone can be shielded from contact with gas samples and can therefore be used as a control or reference to specifically control for sensor drift which may occur between the time of manufacturing and the time of use of the disposable sensor element. In some embodiments, such as in the case of the use of an inert gas or liquid, the discrete binding detector can also include a barrier layer 808, which can be a layer of a polymeric material, a foil, or the like. In some cases, the barrier layer 808 can be removed just prior to use.

In an embodiment, a method for detecting one or more analytes is included. The method can include collecting a gaseous sample from a patient. In some embodiments the gaseous sample can include exhaled breath. In other embodiments, the gaseous sample can include breath removed from the lungs of a patient via a catheter or other similar extraction device. In some embodiments, the extraction device can include an endoscope, a bronchoscope, or tracheoscope. The method can also include contacting a graphene varactor with the gaseous sample, where the graphene varactor includes a graphene layer and a self-assembled monolayer disposed on an outer surface of the graphene layer through electrostatic interactions. In some embodiments, the self-assembled monolayer can provide a Langmuir theta value of at least 0.9. In some embodiments, the method can include selecting derivatized graphene layers that exhibit a Langmuir theta value of at least 0.98.

Langmuir theta values will be discussed more fully below. In some embodiments, the method can include measuring a differential response in a capacitance of the graphene reactor due to the binding of one or more analytes present in the gaseous sample, which in turn can be used to identify disease states. In some embodiments, the method can include a self-assembled monolayer selected from at least one substituted porphyrin or substituted metalloporphyrin, or derivatives thereof.

Graphene Varactors

The graphene varactors described herein can be used to sense one or more analytes in a gaseous sample, such as, for example, the breath of a patient. Graphene varactors embodied herein can exhibit a high sensitivity for volatile organic compounds (VOCs) found in gaseous samples at or near parts-per-million (ppm) or parts-per-billion (ppb) levels. The adsorption of VOCs onto the surface of graphene varactors can change the resistance, capacitance, or quantum capacitance of such devices, and can be used to detect the VOCs and/or patterns of binding by the same that, in turn, can be used to identify disease states such as cancer, cardiac diseases, infections, multiple sclerosis, Alzheimer's disease, Parkinson's disease, and the like. The graphene varactors can be used to detect individual analytes in gas mixtures, as well as patterns of responses in highly complex mixtures. In some embodiments, one or more graphene varactors can be included to detect the same analyte in a gaseous sample. In some embodiments, one or more graphene varactors can be included to detect different analytes in a gaseous sample. In some embodiments, one or more graphene varactors can be included to detect a multitude of analytes in a gaseous sample.

An exemplary graphene varactor can include a graphene layer and a self-assembled monolayer disposed on an outer surface of the graphene layer, interacting with the latter through electrostatic interactions, as shown and discussed above in reference to FIG. 2. The self-assembled monolayers suitable for use herein can provide a Langmuir theta value of at least 0.9. Determination of the Langmuir theta value for a particular self-assembled monolayer using Langmuir adsorption theory is described more fully below. In some embodiments, the self-assembled monolayers suitable for use herein provide a Langmuir theta value of at least 0.95. In some embodiments, the self-assembled monolayers suitable for use herein provide a Langmuir theta value of at least 0.98.

The graphene varactors described herein can include those in which a single graphene layer has been surface-modified through non-covalent electrostatic interactions with one or more substituted porphyrins or substituted metalloporphyrins, as described elsewhere herein. Substituted porphyrins or substituted metalloporphyrins suitable for use herein can be substituted with any number of functional groups described below, including, but not limited to alkyl groups, alkenyl groups, heteroalkyl groups, heteroalkenyl groups, aryl groups, heteroaryl groups, biphenyl groups, substituted biphenyl groups, substituted aryl groups, and/or substituted heteroaryl groups.

In some embodiments, the substituted porphyrins and substituted metalloporphyrins herein can be substituted with any of the following functional groups at anywhere from 1 to 12 positions about the porphyrin or metalloporphyrin ring structure, or more, as is the case for an expanded substituted porphyrin or expanded substituted metalloporphyrin. In some embodiments, an expanded substituted porphyrin or metalloporphyrin can be substituted with any of the following functional groups at anywhere from 1 to greater than 12 positions about the expanded substituted porphyrin or expanded substituted metalloporphyrin ring structure. In some embodiments, the porphyrin or metalloporphyrin ring structure is substituted at only one position about the porphyrin or metalloporphyrin ring structure. In some embodiments, the porphyrin or metalloporphyrin ring structure is substituted at only 2 positions about the porphyrin or metalloporphyrin ring structure. In some embodiments, the substituted porphyrins or substituted metalloporphyrins herein can be substituted at 2, 3, 4, 5, 6, 7, 8, 9, 10, 11, or 12 positions about the porphyrin or metalloporphyrin ring structure.

In some embodiments, the substitutions to the porphyrin or metalloporphyrin ring structures can be symmetrical, whereas in other embodiments the substitutions to the porphyrin or metalloporphyrin ring structures can be asymmetrical. Likewise, in some embodiments, the substitutions to the expanded substituted porphyrin or expanded substituted metalloporphyrin ring structures can be symmetrical, whereas in other embodiments the substitutions to the expanded substituted porphyrin or expanded substituted metalloporphyrin ring structures can be asymmetrical As used herein, the term "alkyl" refers to any linear or branched hydrocarbon functional group containing anywhere from 1 to 50 carbon atoms (i.e., $C_1$-$C_{50}$ alkyl). In some embodiments, the alkyl groups herein can contain any linear or branched hydrocarbon functional group containing anywhere from 6 to 32 carbon atoms (i.e., $C_6$-$C_{32}$ alkyl). In other embodiments, the alkyl groups herein can contain any linear or branched hydrocarbon functional group containing anywhere from 12 to 26 carbon atoms (i.e., $C_{12}$-$C_{26}$ alkyl). The alkyl groups described herein have the general formula $C_nH_{2n+1}$, unless otherwise indicated.

As used herein, the term "alkenyl" refers to any linear or branched hydrocarbon functional group containing anywhere from 1 to 50 carbon atoms, wherein the alkenyl group contains at least one carbon-carbon double bond (i.e., $C_1$-$C_{50}$ alkenyl). In some embodiments, the alkenyl groups herein can contain any linear or branched hydrocarbon functional group containing anywhere from 6 to 32 carbon atoms, wherein the alkenyl group contains at least one carbon-carbon double bond (i.e., $C_6$-$C_{32}$ alkenyl). In other embodiments, the alkenyl groups herein can contain any linear or branched hydrocarbon functional group containing anywhere from 12 to 26 carbon atoms, wherein the alkenyl group contains at least one carbon-carbon double bond (i.e., $C_{12}$-$C_{26}$ alkenyl). The alkenyl groups described herein have the general formula $C_nH_{(2n+1-2x)}$, where x is the number of double bonds present in the alkenyl group, unless otherwise indicated.

As used herein, the term "alkynyl" refers to any linear or branched hydrocarbon functional group containing anywhere from 1 to 50 carbon atoms, including one or more carbon-carbon triple bonds (i.e., $C_1$-$C_{50}$ alkynyl). In some embodiments, the alkynyl groups herein can contain any linear or branched hydrocarbon functional group containing anywhere from 6 to 32 carbon atoms, including one or more carbon-carbon triple bonds (i.e., $C_6$-$C_{32}$ alkynyl). In other embodiments, the alkynyl groups herein can contain any linear or branched hydrocarbon functional group containing anywhere from 12 to 26 carbon atoms, including one or more carbon-carbon triple bonds (i.e., $C_{12}$-$C_{26}$ alkynyl).

As used herein, the term "heteroalkyl" refers to any linear or branched hydrocarbon functional group containing anywhere from 1 to 50 carbon atoms, and one or more heteroatoms, including, but not limited to, N, O, P, S, Si, Se, and B, or any combination thereof (i.e., $C_1$-$C_{50}$ heteroalkyl). In some embodiments, the heteroalkyl groups herein can contain any linear or branched hydrocarbon functional group containing anywhere from 6 to 32 carbon atoms and one or more heteroatoms, including, but not limited to, N, O, P, S, Si, Se, and B, or any combination thereof (i.e., $C_6$-$C_{32}$ heteroalkyl). In other embodiments, the heteroalkyl groups herein can contain any linear or branched hydrocarbon functional group containing anywhere from 12 to 26 carbon atoms and one or more heteroatoms, including, but not limited to, N, O, P, S, Si, Se, and B, or any combination thereof (i.e., $C_{12}$-$C_{26}$ heteroalkyl). In some embodiments, the heteroalkyl groups herein can have the general formula —RZR, —ZRZR, or —RZRZR, where R can include, but not be limited to, any identical or different, linear or branched, $C_1$-$C_{50}$ alkyl, or a combination thereof; and Z can include one or more heteroatoms including, but not limited to, N, O, P, S, Si, Se, and B, or any combination thereof.

In some embodiments, the heteroalkyl group can include, but not limited to, alkoxy groups, alkyl amide groups, alkyl thioether groups, alkyl ester groups, and the like. Examples of heteroalkyl groups suitable for use herein can include, but not be limited to, those selected from —ROH, —RC(O)OH, —RC(O)OR, —ROR, —RSR, —RCHO, —RX, —RC(O)NH$_2$, —RC(O)NR, —RNH$_3^+$, —RNH$_2$, —RNO$_2$, —RNR, —RNRR, —RB(OH)$_2$, or any combination thereof; where R can include, but not be limited to, any identical or different, linear or branched, $C_1$-$C_{50}$ alkyl, or a combination thereof; and X can be a halogen including F, Cl, Br, I, or At.

As used herein, the term "heteroalkenyl" refers to any linear or branched hydrocarbon functional group containing anywhere from 1 to 50 carbon atoms, including one or more carbon-carbon double bonds, and one or more heteroatoms including, but not limited to, N, O, P, S, Si, Se, and B, or any combination thereof (i.e., $C_1$-$C_{50}$ heteroalkenyl). In some embodiments, the heteroalkenyl groups herein can contain any linear or branched hydrocarbon functional group containing anywhere from 6 to 32 carbon atoms, including one or more carbon-carbon double bonds, and one or more heteroatoms, including, but not limited to, N, O, P, S, Si, Se, and B, or any combination thereof (i.e., $C_6$-$C_{32}$ heteroalkenyl). In other embodiments, the heteroalkenyl groups herein can contain any linear or branched hydrocarbon functional group containing anywhere from 12 to 26 carbon atoms, including one or more carbon-carbon double bonds, and one or more heteroatoms, including, but not limited to, N, O, P, S, Si, Se, and B, or any combination thereof (i.e., $C_{12}$-$C_{26}$ heteroalkenyl). In some embodiments, the heteroalkenyl groups herein can have the general formula —RZR, —ZRZR, or —RZRZR, where R can include, but not be limited to, any identical or different, linear or branched, $C_1$-$C_{50}$ alkyl or $C_1$-$C_{50}$ alkenyl, provided that at least one carbon-carbon double bond is present in at least one R group, or a combination thereof; and Z can include one or more heteroatoms including, but not limited to, N, O, P, S, Si, Se, and B, or any combination thereof.

In some embodiments, the heteroalkenyl group can include, but not limited to, alkenoxy groups, alkenyl amines, alkenyl thioester groups, alkenyl ester groups, and the like. Examples of heteroalkenyl groups suitable for use herein can include, but not be limited to, those selected from —ROH, —RC(O)OH, —RC(O)OR, —ROR, —RSR, —RCHO, —RX, —RC(O)NH$_2$, —RC(O)NR, —RNH$_3^+$, —RNH$_2$, —RNO$_2$, —RNR, —RNRR, —RB(OH)$_2$, or any combination thereof; where R can include, but not be limited to, any identical or different, linear or branched, $C_1$-$C_{50}$ alkenyl, or a combination thereof; and X can be a halogen including F, Cl, Br, I, or At.

As used herein, the term "heteroalkynyl" refers to any linear or branched hydrocarbon functional group containing anywhere from 1 to 50 carbon atoms, including one or more carbon-carbon triple bonds, and one or more heteroatoms including, but not limited to, N, O, P, S, Si, Se, and B, or any combination thereof (i.e., $C_1$-$C_{50}$ heteroalkynyl). In some embodiments, the heteroalkynyl groups herein can contain any linear or branched hydrocarbon functional group containing anywhere from 6 to 32 carbon atoms, including one or more carbon-carbon triple bonds, and one or more heteroatoms, including, but not limited to, N, O, P, S, Si, Se, and B, or any combination thereof (i.e., $C_6$-$C_{32}$ heteroalkynyl). In other embodiments, the heteroalkynyl groups herein can contain any linear or branched hydrocarbon functional group containing anywhere from 12 to 26 carbon atoms, including one or more carbon-carbon triple bonds, and one or more heteroatoms, including, but not limited to, N, O, P, S, Si, Se, and B, or any combination thereof (i.e., $C_{12}$-$C_{26}$ heteroalkynyl). In some embodiments, the heteroalkynyl groups herein can have the general formula —RZR, —ZRZR, or —RZRZR, where R can include, but not be limited to, any identical or different, linear or branched, $C_1$-$C_{50}$ alkyl, $C_1$-$C_{50}$ alkenyl, or $C_1$-$C_{50}$ alkynyl, provided that at least one carbon-carbon triple bond is present in at least one R group or a combination thereof; and Z can include one or more heteroatoms including, but not limited to, N, O, P, S, Si, Se, and B, or any combination thereof.

In some embodiments, the heteroalkynyl group can include, but not limited to, alkynyloxy groups, alkynyl amines, alkynyl thioester groups, alkynyl ester groups, and the like. Examples of heteroalkynyl groups suitable for use herein can include, but not be limited to, those selected from —ROH, —RC(O)OH, —RC(O)OR, —ROR, —RSR, —RCHO, —RX, —RC(O)NH$_2$, —RC(O)NR, —RNH$_3^+$, —RNH$_2$, —RNO$_2$, —RNR, —RNRR, —RB(OH)$_2$, or any combination thereof; where R can include, but not be limited to, any identical or different, linear or branched, $C_1$-$C_{50}$ alkynyl, or a combination thereof; and X can be a halogen including F, Cl, Br, I, or At.

As used herein, the term "biphenyl" refers to an aromatic hydrocarbon functional group with the molecular formula $(C_6H_5)_2$, and when bound to a porphyrin or metalloporphyrin has one less hydrogen at the site of covalent attachment to the porphyrin or metalloporphyrin ring structure. In some embodiments, the biphenyl functional group can be substituted to form a substituted biphenyl functional group. As used herein, the term "substituted biphenyl" refers to a biphenyl functional group, as described, which itself is substituted with one or more alkyl, alkenyl, alkynyl, heteroalkyl, heteroalkenyl, or heteroalkynyl functional groups, or any combination thereof, as described herein.

As used herein, the term "aryl" refers to any aromatic hydrocarbon functional group containing a $C_5$- to $C_8$-membered aromatic ring, such as, for example, cyclopentadiene, benzene, and derivatives thereof. The corresponding aromatic radicals to the examples provided include, for example, cyclopentadienyl and phenyl radicals, and derivatives thereof. In some embodiments, the aryl functional groups herein can be further substituted to form substituted aryl functional groups. As used herein, the term "substituted aryl" refers to any aromatic hydrocarbon functional group containing a $C_5$- to $C_8$-membered aromatic ring, which itself can be substituted with one or more alkyl, alkenyl, alkynyl, heteroalkyl, heteroalkenyl, or heteroalkynyl functional groups, or any combination thereof, as described herein.

In some embodiments, the aryl functional groups herein can be substituted to form aryloxy functional groups. As used herein, the term "aryloxy" can include a functional group of the general formula Aryl-O—, where the aryl functional group can include a $C_5$- to $C_8$-membered aromatic ring. In some embodiments, the aryloxy group can include a phenoxy functional group of the formula $C_6H_5O$—. In some embodiments, the aryloxy functional group can be further substituted. As used herein, the term "substituted aryloxy" can include any aryloxy functional group, as defined herein, which is further substituted with one or more alkyl, alkenyl, alkynyl, heteroalkyl, heteroalkenyl, or heteroalkynyl functional groups, or any combination thereof, as described herein.

In some embodiments, the aryl functional groups herein can be substituted to form arylthio functional groups. As used herein, the term "arylthio" can include a functional group of the general formula Aryl-S—, where the aryl functional group can include a $C_5$- to $C_8$-membered aromatic ring. In some embodiments, the arylthio functional group can include a phenylsulfanyl functional group of the formula $C_6H_5S$—. In some embodiments, the arylthio functional group can be further substituted. As used herein, the term "substituted arylthio" can include any arylthio functional group, as defined herein, which is further substituted with one or more alkyl, alkenyl, alkynyl, heteroalkyl, heteroalkenyl, or heteroalkynyl functional groups, or any combination thereof, as described herein.

In some embodiments, the aryl functional groups herein can be substituted to form arylamine functional groups. As used herein, the term "arylamine" can include a functional group of the general formula Aryl-$NH_n$, where the aryl functional group can include a $C_5$- to $C_8$-membered aromatic ring, and n can be from 0 to 3, providing that when n=0, 1, or 2, a non-H substitution is present on the N atom, which can include, but is not to be limited to, one or more alkyl, alkenyl, alkynyl, heteroalkyl, heteroalkenyl, or heteroalkynyl functional groups, or any combination thereof, as described herein.

In some embodiments, the arylamine functional group can include a $\lambda^1$-azanylbenzene functional group of the formula $C_6H_5N$. In some embodiments, the arylamine functional group can be further substituted. As used herein, the term "substituted arylamine" can include any arylamine functional group, as defined herein, which is further substituted with one or more alkyl, alkenyl, alkynyl, heteroalkyl, heteroalkenyl, or heteroalkynyl functional groups, or any combination thereof, as described herein.

In some embodiments, the aryl functional groups herein can include one or more heteroatoms to form heteroaryl functional groups. Suitable heteroatoms for use herein can include, but not be limited to, N, O, P, S, Si, Se, and B. As used herein, the term "heteroaryl" refers to any aryl functional group, as defined herein, where one or more carbon atoms of the $C_5$- to $C_8$-membered aromatic ring has been replaced with one or more heteroatoms or combinations of heteroatoms. Examples of heteroaryl functional groups can include, but not be limited to radicals of, pyrrole, thiophene, furan, imidazole, pyridine, and pyrimidine. The heteroaryl functional groups herein can be further substituted to form substituted heteroaryl functional groups. As used herein, the term "substituted heteroaryl" refers to any heteroaryl functional group, as described herein, which is further substituted with one or more alkyl, alkenyl, alkynyl, heteroalkyl, heteroalkenyl, or heteroalkynyl functional groups, or any combination thereof, as described herein.

In some embodiments, the substituted porphyrins herein can include those having the general formula (1):

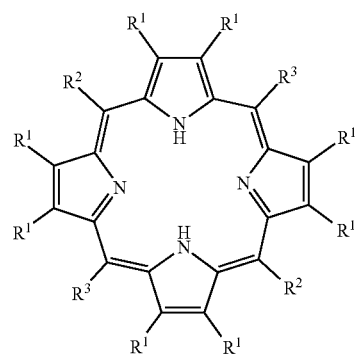

where each $R^1$ is independently —H; —X, where X is a halogen atom; any linear or branched $C_1$-$C_{50}$ alkyl, $C_1$-$C_{50}$ alkenyl, $C_1$-$C_{50}$ alkynyl, $C_1$-$C_{50}$ heteroalkyl, $C_1$-$C_{50}$ heteroalkenyl, $C_1$-$C_{50}$ heteroalkynyl, or any combination thereof; —RZR, —ZRZR, or —RZRZR, where R can include, but not be limited to, any identical or different, linear or branched, $C_1$-$C_{50}$ alkyl, $C_1$-$C_{50}$ alkenyl, $C_1$-$C_{50}$ alkynyl, or any combination thereof, and Z can be one or more heteroatom selected from N, O, P, S, Se, or Si; —ROH, —RC(O)OH, —RC(O)OR, —ROR, —RSR, —RCHO, —RX, —RC(O)$NH_2$, —RC(O)NR, —$RNH_3^+$, —$RNH_2$, —$RNO_2$, —RNR, —RNRR, —RB(OH)$_2$, or any combination thereof, where R can include, but is not to be limited to, any identical or different, linear, branched, or cyclic $C_1$-$C_{50}$ alkyl, $C_1$-$C_{50}$ alkenyl, $C_1$-$C_{50}$ alkynyl, or a combination thereof, or can be absent such that the remaining portion of the functional group is covalently bound directly to one or more carbon atoms of the substituted porphyrin; and where each $R^2$ and $R^3$ are independently —H; any linear or branched $C_1$-$C_{50}$ alkyl, $C_1$-$C_{50}$ alkenyl, $C_1$-$C_{50}$ alkynyl, $C_1$-$C_{50}$ heteroalkyl, $C_1$-$C_{50}$ heteroalkenyl, $C_1$-$C_{50}$ heteroalkynyl or any combination thereof; —RZR or —RZRZR, where R can include, but not be limited to, any identical or different, linear or branched, $C_1$-$C_{50}$ alkyl, $C_1$-$C_{50}$ alkenyl, $C_1$-$C_{50}$ alkynyl, or any combination thereof, and Z can be one or more heteroatom selected from N, O, P, S, Se, or Si; an aryl, heteroaryl, substituted aryl, or substituted heteroaryl; a biphenyl or substituted biphenyl; an aryloxy, arylthio, arylamine, or any substitutions thereof; or any combination thereof; and where every $R^1$, $R^2$, and $R^3$ group is covalently bound directly to the substituted porphyrin.

In some embodiments, the $R^2$ and $R^3$ groups are the same, while in other embodiments the $R^2$ and $R^3$ groups are different.

In some embodiments, the substituted porphyrins can include those having the general formula (2):

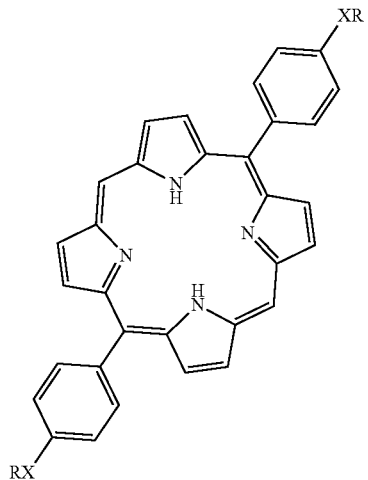

where each X is independently a heteroatom selected from N, O, P, S, Se, or Si, or absent, such that R is covalently attached to the phenyl group; and where each R is independently —H; any linear or branched $C_1$-$C_{50}$ alkyl, $C_1$-$C_{50}$ alkenyl, $C_1$-$C_{50}$ alkynyl, $C_1$-$C_{50}$ heteroalkyl, $C_1$-$C_{50}$ heteroalkenyl, $C_1$-$C_{50}$ heteroalkynyl or any combination thereof; —RZR, —ZRZR, or —RZRZR, where R can include, but not be limited to, any identical or different, linear or branched, $C_1$-$C_{50}$ alkyl, $C_1$-$C_{50}$ alkenyl, $C_1$-$C_{50}$ alkynyl, or any combination thereof, and Z can be one or more heteroatom selected from N, O, P, S, Se, or Si; an aryl, heteroaryl, substituted aryl, or substituted heteroaryl; a biphenyl or substituted biphenyl; an aryloxy, arylthio, arylamine, or any substitutions thereof; or any combination thereof.

In some embodiments, the substituted porphyrins can include those having the general formula (3):

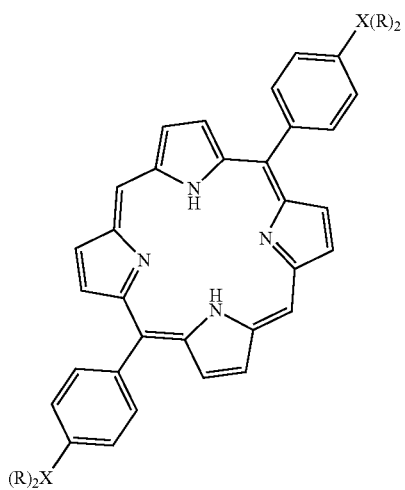

where each X is independently a heteroatom, including, but not limited to N, O, P, S, Se, or Si; and where each R is independently —H; any linear or branched $C_1$-$C_{50}$ alkyl, $C_1$-$C_{50}$ alkenyl, $C_1$-$C_{50}$ alkynyl, $C_1$-$C_{50}$ heteroalkyl, $C_1$-$C_{50}$ heteroalkenyl, $C_1$-$C_{50}$ heteroalkynyl or any combination thereof; —RZR, —ZRZR, or —RZRZR, where R can include, but not be limited to, any identical or different, linear or branched, $C_1$-$C_{50}$ alkyl, $C_1$-$C_{50}$ alkenyl, $C_1$-$C_{50}$ alkynyl, or any combination thereof, and Z can be one or more heteroatom selected from N, O, P, S, Se, or Si; an aryl, heteroaryl, substituted aryl, or substituted heteroaryl; a biphenyl or substituted biphenyl; an aryloxy, arylthio, arylamine, or any substitutions thereof; or one R group can be absent; or any combination thereof.

In some embodiments, suitable substituted porphyrins for use herein can include those having formulas (4) through (9) as shown in TABLE 1.

TABLE 1

Substituted Porphyrins

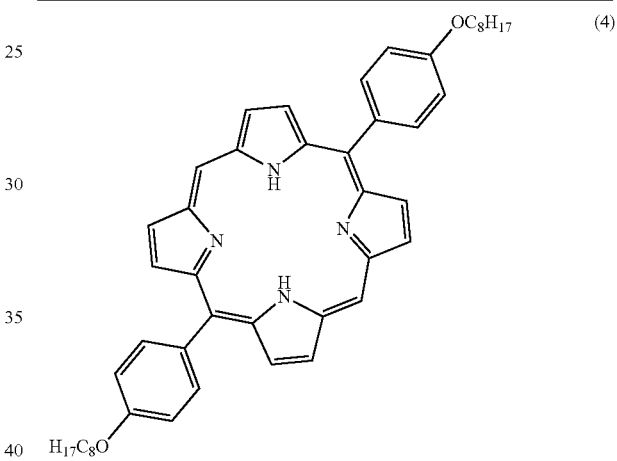

(4)

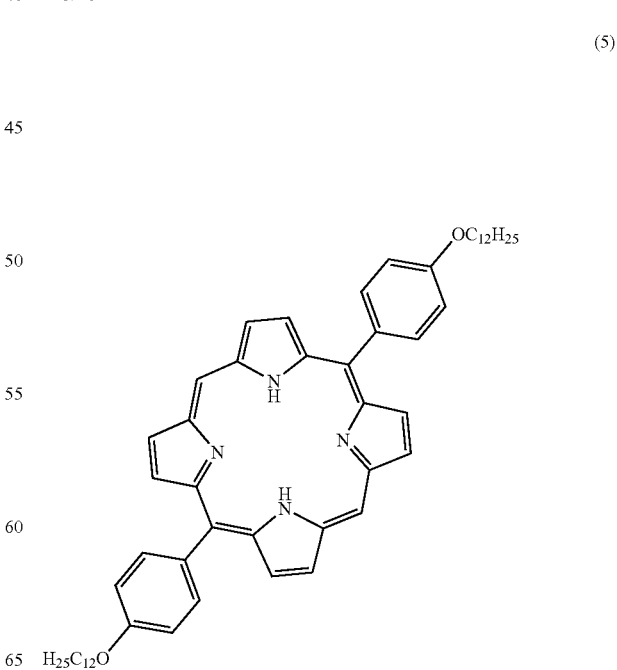

(5)

TABLE 1-continued

Substituted Porphyrins

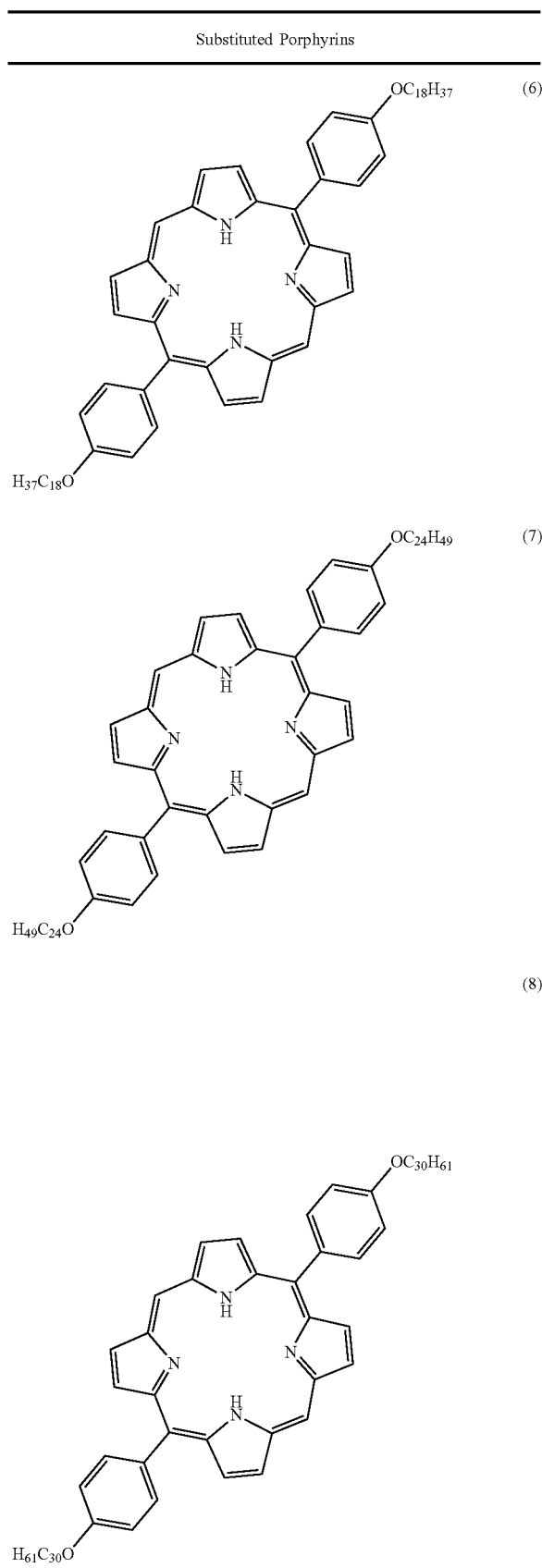

In some embodiments, the substituted porphyrins can include those having phthalocyanine substitutions in the place of one or more of the pyrrole subunits of the porphyrin ring structure of formula (1). The phthalocyanine-substituted porphyrins suitable for use herein include those having the general formulas (10) through (14), as shown in TABLE 2.

TABLE 2

Phthalocyanine-substituted porphyrins

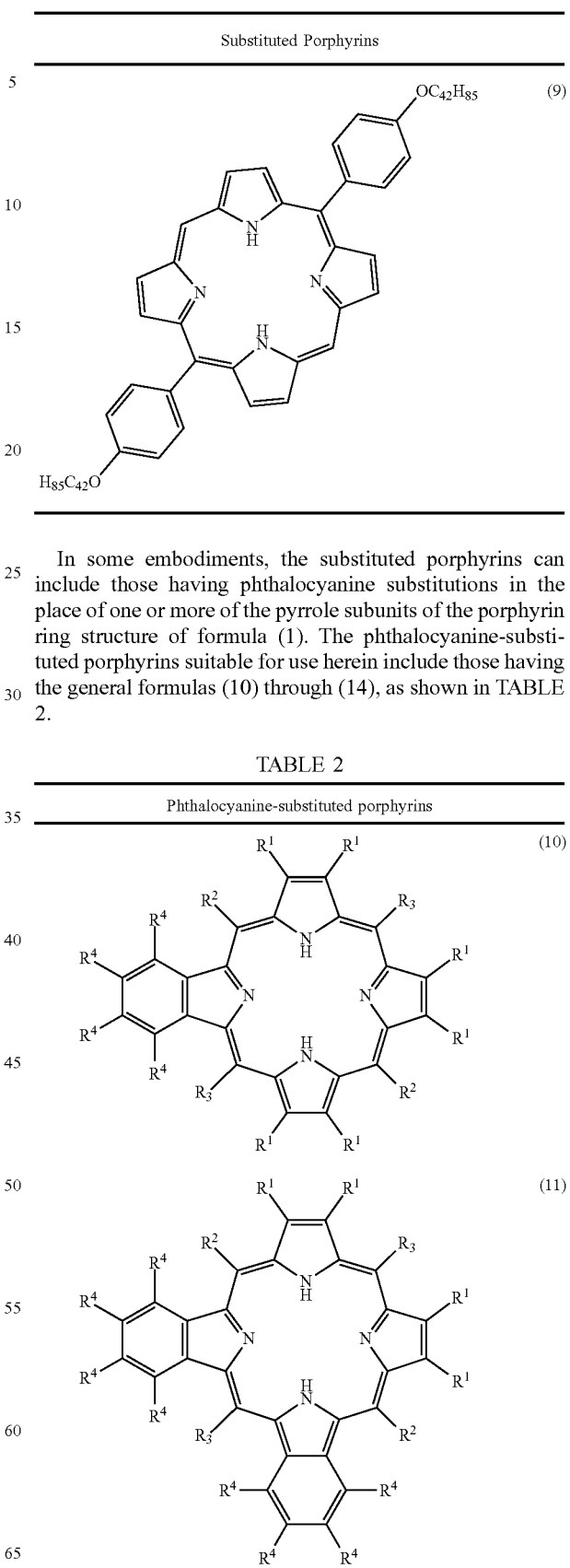

TABLE 2-continued

Phthalocyanine-substituted porphyrins

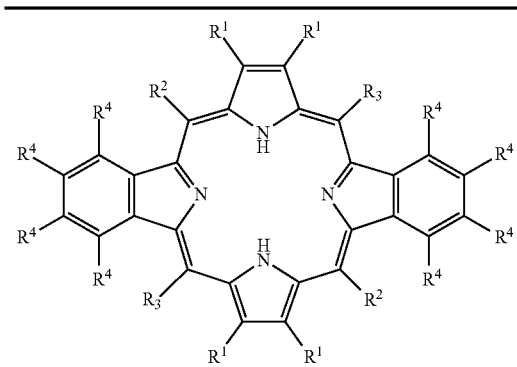
(12)

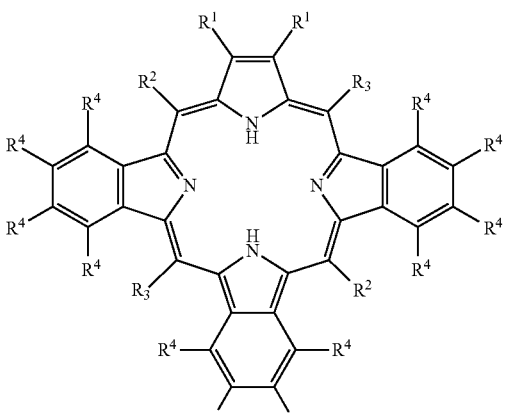
(13)

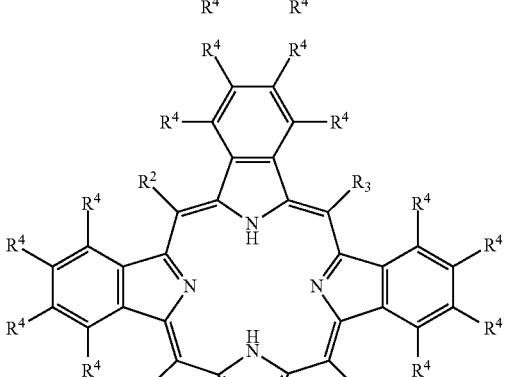
(14)

where each $R^1$ and $R^4$ are independently —H; —X, where X is a halogen atom; any linear or branched $C_1$-$C_{50}$ alkyl, $C_1$-$C_{50}$ alkenyl, $C_1$-$C_{50}$ alkynyl, $C_1$-$C_{50}$ heteroalkyl, $C_1$-$C_{50}$ heteroalkenyl, $C_1$-$C_{50}$ heteroalkynyl, or any combination thereof; —RZR, —ZRZR, or —RZRZR, where R can include, but not be limited to, any identical or different, linear or branched, $C_1$-$C_{50}$ alkyl, $C_1$-$C_{50}$ alkenyl, or $C_1$-$C_{50}$ alkynyl, and Z can be one or more heteroatom selected from N, O, P, S, Se, or Si; —ROH, —RC(O)OH, —RC(O)OR, —ROR, —RSR, —RCHO, —RX, —RC(O)NH$_2$, —RC(O)NR, —RNH$_3^+$, —RNH$_2$, —RNO$_2$, —RNR, —RNRR, —RB(OH)$_2$, or any combination thereof, where R can include, but is not be limited to, any identical or different, linear, branched, or cyclic $C_1$-$C_{50}$ alkyl, $C_1$-$C_{50}$ alkenyl, $C_1$-$C_{50}$ alkynyl, or a combination thereof, or can be absent such that the remaining portion of the functional group is covalently bound directly to one or more carbon atoms of the phthalocyanine-substituted porphyrin; and where $R^2$ and $R^3$ are independently —H; any linear or branched $C_1$-$C_{50}$ alkyl, $C_1$-$C_{50}$ alkenyl, $C_1$-$C_{50}$ alkynyl, $C_1$-$C_{50}$ heteroalkyl, $C_1$-$C_{50}$ heteroalkenyl, $C_1$-$C_{50}$ heteroalkynyl, or any combination thereof; —RZR, —ZRZR, or —RZRZR, where R can include, but not be limited to, any identical or different, linear or branched, $C_1$-$C_{50}$ alkyl, $C_1$-$C_{50}$ alkenyl, $C_1$-$C_{50}$ alkynyl, or a combination thereof, and Z can be one or more heteroatom selected from N, O, P, S, Se, or Si; an aryl, heteroaryl, substituted aryl, or substituted heteroaryl; a biphenyl or substituted biphenyl; an aryloxy, arylthio, arylamine, or any substitutions thereof; or any combination thereof; and where every $R^1$, $R^2$, $R^3$, and $R^4$ group is covalently bound directly to the phthalocyanine-substituted porphyrin.

In some embodiments, the $R^2$ and $R^3$ groups are the same, while in other embodiments the $R^2$ and $R^3$ groups are different.

In some embodiments, the substituted porphyrins herein can include one or more expanded substituted porphyrins. As used herein, the term "expanded substituted porphyrin" refers to a porphyrin having an expanded ring structure including more than the four pyrrole rings associated with the structure shown in formula (1). In some embodiments, the expanded substituted porphyrin can include 5 modified pyrrole subunits, each connected by a methine (=CH—) bridge. In some embodiments, the expanded substituted porphyrin ring structure can include 6 modified pyrrole subunits, each connected by a methine (=CH—) bridge. In some embodiments, the expanded substituted porphyrin ring structure can include more than 6 modified pyrrole subunits, each connected by a methine (=CH—) bridge. Exemplary expanded substituted porphyrin molecules include, but are not to be limited to, those expanded substituted porphyrin molecules having the general formulas (15) and (16) as shown in TABLE 3.

TABLE 3

Expanded Substituted Porphyrins

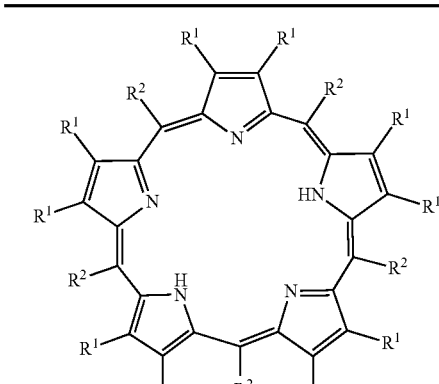
(15)

TABLE 3-continued

Expanded Substituted Porphyrins

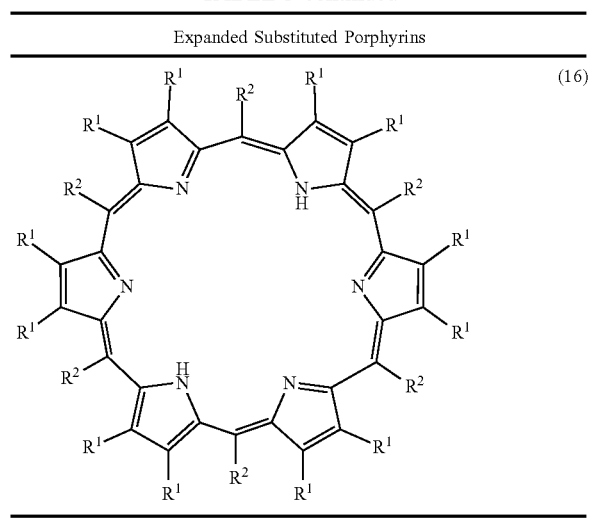

(16)

where each $R^1$ is independently —H; —X, where X is a halogen atom; any linear or branched $C_1$-$C_{50}$ alkyl, $C_1$-$C_{50}$ alkenyl, $C_1$-$C_{50}$ alkynyl, $C_1$-$C_{50}$ heteroalkyl, $C_1$-$C_{50}$ heteroalkenyl, $C_1$-$C_{50}$ heteroalkynyl, or any combination thereof; —RZR, —ZRZR, or —RZRZR, where R can include, but not be limited to, any identical or different, linear or branched, $C_1$-$C_{50}$ alkyl, $C_1$-$C_{50}$ alkenyl, $C_1$-$C_{50}$ alkynyl, or any combination thereof, and Z can be one or more heteroatom selected from N, O, P, S, Se, or Si; —ROH, —RC(O)OH, —RC(O)OR, —ROR, —RSR, —RCHO, —RX, —RC(O)NH$_2$, —RC(O)NR, —RNH$_3^+$, —RNH$_2$, —RNO$_2$, —RNR, —RNRR, —RB(OH)$_2$, or any combination thereof, where R can include, but is not to be limited to, any identical or different, linear, branched, or cyclic $C_1$-$C_{50}$ alkyl, $C_1$-$C_{50}$ alkenyl, $C_1$-$C_{50}$ alkynyl, or a combination thereof, or can be absent such that the remaining portion of the functional group is covalently bound directly to one or more carbon atoms of the expanded substituted porphyrin; and where $R^2$ is independently —H; any linear or branched $C_1$-$C_{50}$ alkyl, $C_1$-$C_{50}$ alkenyl, $C_1$-$C_{50}$ alkynyl, $C_1$-$C_{50}$ heteroalkyl, $C_1$-$C_{50}$ heteroalkenyl, $C_1$-$C_{50}$ heteroalkynyl or any combination thereof; —RZR or —RZRZR, where R can include, but not be limited to, any identical or different, linear or branched, $C_1$-$C_{50}$ alkyl, $C_1$-$C_{50}$ alkenyl, $C_1$-$C_{50}$ alkynyl, or any combination thereof, and Z can be one or more heteroatom selected from N, O, P, S, Se, or Si; an aryl, heteroaryl, substituted aryl, or substituted heteroaryl; a biphenyl or substituted biphenyl; an aryloxy, arylthio, arylamine, or any substitutions thereof; or any combination thereof; and where every $R^1$ are $R^2$ groups are covalently bound directly to the expanded substituted porphyrin.

It will be appreciated that the expanded substituted porphyrin ring structures described herein can further include those having phthalocyanine substitutions in the place of one or more of the pyrrole subunits of the porphyrin ring structures of formulas (15) and (16).

In some embodiments, the graphene varactors described herein can include those in which a single graphene layer has been surface-modified through non-covalent electrostatic interactions between the graphene layer and substituted metalloporphyrins. In some embodiments, the substituted metalloporphyrins herein can include those having the general formula (17):

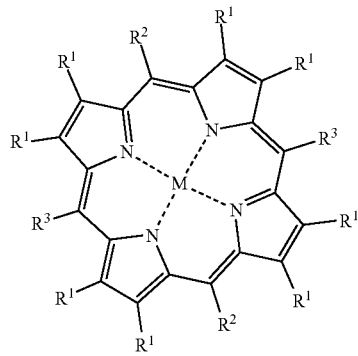

where each $R^1$ is independently —H; —X, where X is a halogen atom; any linear or branched $C_1$-$C_{50}$ alkyl, $C_1$-$C_{50}$ alkenyl, $C_1$-$C_{50}$ alkynyl, $C_1$-$C_{50}$ heteroalkyl, $C_1$-$C_{50}$ heteroalkenyl, $C_1$-$C_{50}$ heteroalkynyl, or any combination thereof; —RZR, —ZRZR, or —RZRZR, where R can include, but not be limited to, any identical or different, linear or branched, $C_1$-$C_{50}$ alkyl, $C_1$-$C_{50}$ alkenyl, $C_1$-$C_{50}$ alkynyl, or any combination thereof, and Z can be one or more heteroatom selected from N, O, P, S, Se, or Si; —ROH, —RC(O)OH, —RC(O)OR, —ROR, —RSR, —RCHO, —RX, —RC(O)NH$_2$, —RC(O)NR, —RNH$_3^+$, —RNH$_2$, —RNO$_2$, —RNR, —RNRR, —RB(OH)$_2$, or any combination thereof, where R can include, but is not to be limited to, any identical or different, linear, branched, or cyclic $C_1$-$C_{50}$ alkyl, $C_1$-$C_{50}$ alkenyl, $C_1$-$C_{50}$ alkynyl, or a combination thereof, or can be absent such that the remaining portion of the functional group is covalently bound directly to one or more carbon atoms of the substituted metalloporphyrin; and where $R^2$ and $R^3$ are independently —H; any linear or branched $C_1$-$C_{50}$ alkyl, $C_1$-$C_{50}$ alkenyl, $C_1$-$C_{50}$ alkynyl, $C_1$-$C_{50}$ heteroalkyl, $C_1$-$C_{50}$ heteroalkenyl, $C_1$-$C_{50}$ heteroalkynyl, or any combination thereof; —RZR, —ZRZR, or —RZRZR, where R can include, but not be limited to, any identical or different, linear or branched, $C_1$-$C_{50}$ alkyl, $C_1$-$C_{50}$ alkenyl, $C_1$-$C_{50}$ alkynyl, or any combination thereof, and Z can be one or more heteroatom selected from N, O, P, S, Se, or Si; an aryl, heteroaryl, substituted aryl, or substituted heteroaryl; a biphenyl or substituted biphenyl; an aryloxy, arylthio, arylamine, or any substitutions thereof; or any combination thereof; and where every $R^1$, $R^2$, and $R^3$ group is covalently bound directly to the substituted metalloporphyrin; and where M is a metal including but not limited to aluminum, calcium, magnesium, manganese, iron, cobalt, nickel, zinc, ruthenium, palladium, silver, platinum, indium, tin, copper, rhodium, chromium, gallium, osmium, iridium, or derivatives thereof; and where the oxidation state of the metal can include, but not be limited to an oxidation state of I, II, III, IV, V, VI, VII, or VIII. In some embodiments, the metal is magnesium. In some embodiments the metal is silver. In some embodiments the metal is platinum. In some embodiments the metal is palladium. In some embodiments the metal is zinc. In some embodiments, various inorganic, organic, ionic, or neutral ligands can be coordinated with the metals herein, including, but not to be limited to, Cl$^-$, F$^-$, Br$^-$, I$^-$, CN$^-$, SCN$^-$, CO, NH$_3$, H$_2$O, NO, CH$_3$NH$_2$, pyridine, and the like. In some embodiments, the number of ligands can be from zero ligands to eight ligands.

In some embodiments, the $R^2$ and $R^3$ groups are the same, while in other embodiments the $R^2$ and $R^3$ groups are different.

In some embodiments, the substituted metalloporphyrins can include those having the general formula (18):

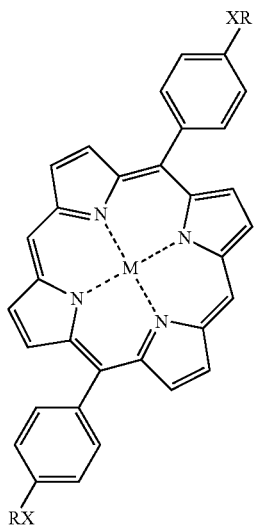

where each X is independently a heteroatom selected from N, O, P, S, Se, or Si, or absent, such that R is covalently attached to the phenyl group; and where each R is independently —H; any linear or branched $C_1$-$C_{50}$ alkyl, $C_1$-$C_{50}$ alkenyl, $C_1$-$C_{50}$ alkynyl, $C_1$-$C_{50}$ heteroalkyl, $C_1$-$C_{50}$ heteroalkenyl, $C_1$-$C_{50}$ heteroalkynyl, or any combination thereof; —RZR, —ZRZR, or —RZRZR, where R can include, but not be limited to, any identical or different, linear or branched, $C_1$-$C_{50}$ alkyl, $C_1$-$C_{50}$ alkenyl, $C_1$-$C_{50}$ alkynyl, or any combination thereof, and Z can be one or more heteroatom selected from N, O, P, S, Se, or Si; an aryl, heteroaryl, substituted aryl, or substituted heteroaryl; a biphenyl or substituted biphenyl; an aryloxy, arylthio, arylamine, or any substitutions thereof; or any combination thereof; and where M is a metal including but not limited to aluminum, calcium, magnesium, manganese, iron, cobalt, nickel, zinc, ruthenium, palladium, silver, platinum, indium, tin, copper, rhodium, chromium, gallium, osmium, iridium, or derivatives thereof; and where the oxidation state of the metal can include, but not be limited to an oxidation state of I, II, III, IV, V, VI, VII, or VIII. In some embodiments, the metal is magnesium. In some embodiments the metal is silver. In some embodiments the metal is platinum. In some embodiments the metal is palladium. In some embodiments the metal is zinc. In some embodiments, various inorganic, organic, ionic, or neutral ligands can be coordinated with the metals herein, including, but not to be limited to, $Cl^-$, $F^-$, $Br^-$, $I^-$, $CN^-$, $SCN^-$, CO, $NH_3$, $H_2O$, NO, $CH_3NH_2$, pyridine, and the like. In some embodiments, the number of ligands can be from zero ligands to eight ligands.

In some embodiments, the substituted metalloporphyrins can include those having the general formula (19):

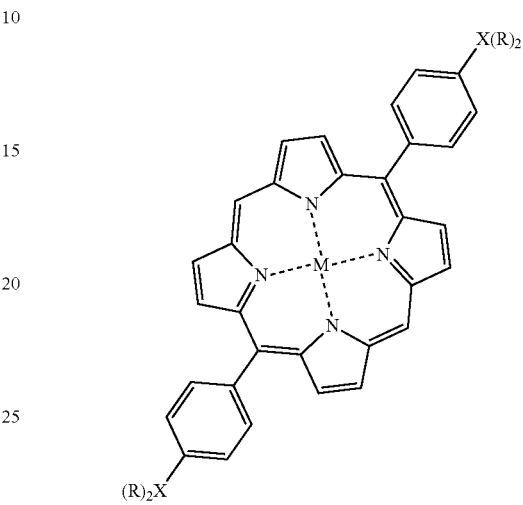

where each X is independently a heteroatom selected from N, O, P, S, Se, or Si; and where each R is independently —H; any linear or branched $C_1$-$C_{50}$ alkyl, $C_1$-$C_{50}$ alkenyl, $C_1$-$C_{50}$ alkynyl, $C_1$-$C_{50}$ heteroalkyl, $C_1$-$C_{50}$ heteroalkenyl, $C_1$-$C_{50}$ heteroalkynyl, or any combination thereof; —RZR, —ZRZR, or —RZRZR, where R can include, but not be limited to, any identical or different, linear or branched, $C_1$-$C_{50}$ alkyl, $C_1$-$C_{50}$ alkenyl, $C_1$-$C_{50}$ alkynyl, or any combination thereof, and Z can be one or more heteroatom selected from N, O, P, S, Se, or Si; an aryl, heteroaryl, substituted aryl, or substituted heteroaryl; a biphenyl or substituted biphenyl; an aryloxy, arylthio, arylamine, or any substitutions thereof; or one R group can be absent; or any combination thereof; and where M is a metal including but not limited to aluminum, calcium, magnesium, manganese, iron, cobalt, nickel, zinc, ruthenium, palladium, silver, platinum, indium, tin, copper, rhodium, chromium, gallium, osmium, iridium, or derivatives thereof; and where the oxidation state of the metal can include, but not be limited to an oxidation state of I, II, III, IV, V, VI, VII, or VIII. In some embodiments, the metal is magnesium. In some embodiments the metal is silver. In some embodiments the metal is platinum. In some embodiments the metal is palladium. In some embodiments the metal is zinc. In some embodiments, various inorganic, organic, ionic, or neutral ligands can be coordinated with the metals herein, including, but not to be limited to, $Cl^-$, $F^-$, $Br^-$, $I^-$, $CN^-$, $SCN^-$, CO, $NH_3$, $H_2O$, NO, $CH_3NH_2$, pyridine, and the like. In some embodiments, the number of ligands can be from zero ligands to eight ligands.

In some embodiments, suitable substituted metalloporphyrins can include those having formulas (20) through (25) as shown in TABLE 4.

TABLE 4

Substituted Metalloporphyrins

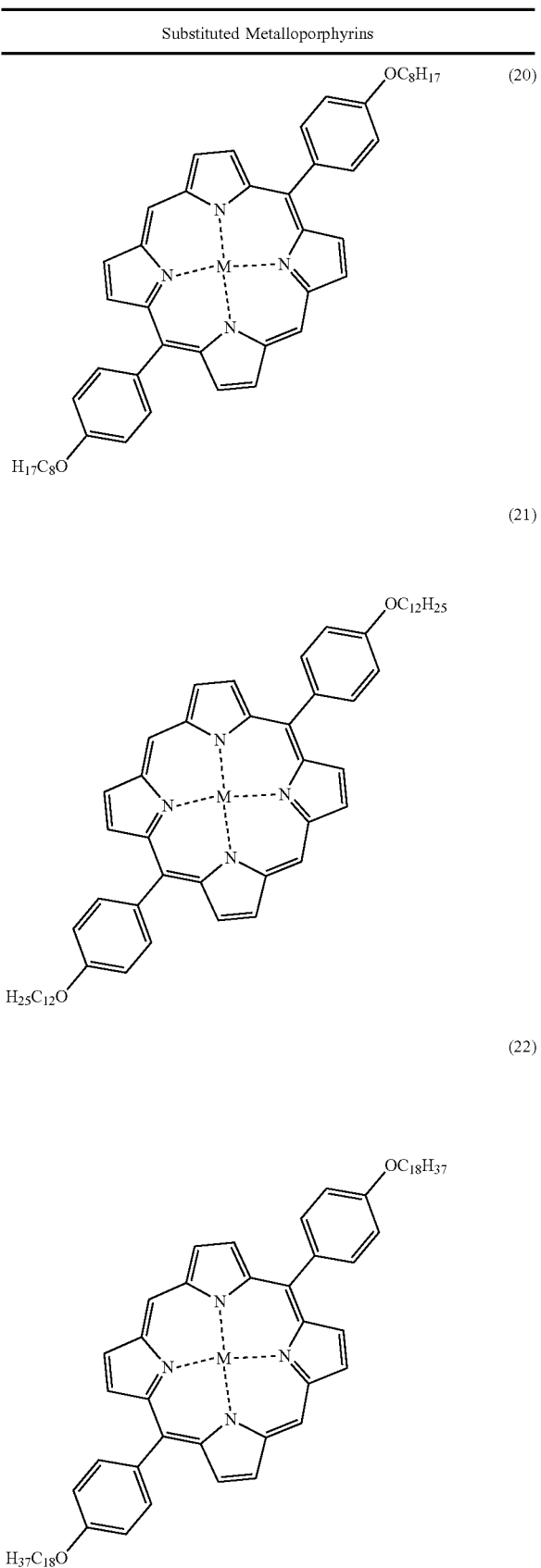

(20), (21), (22)

TABLE 4-continued

Substituted Metalloporphyrins

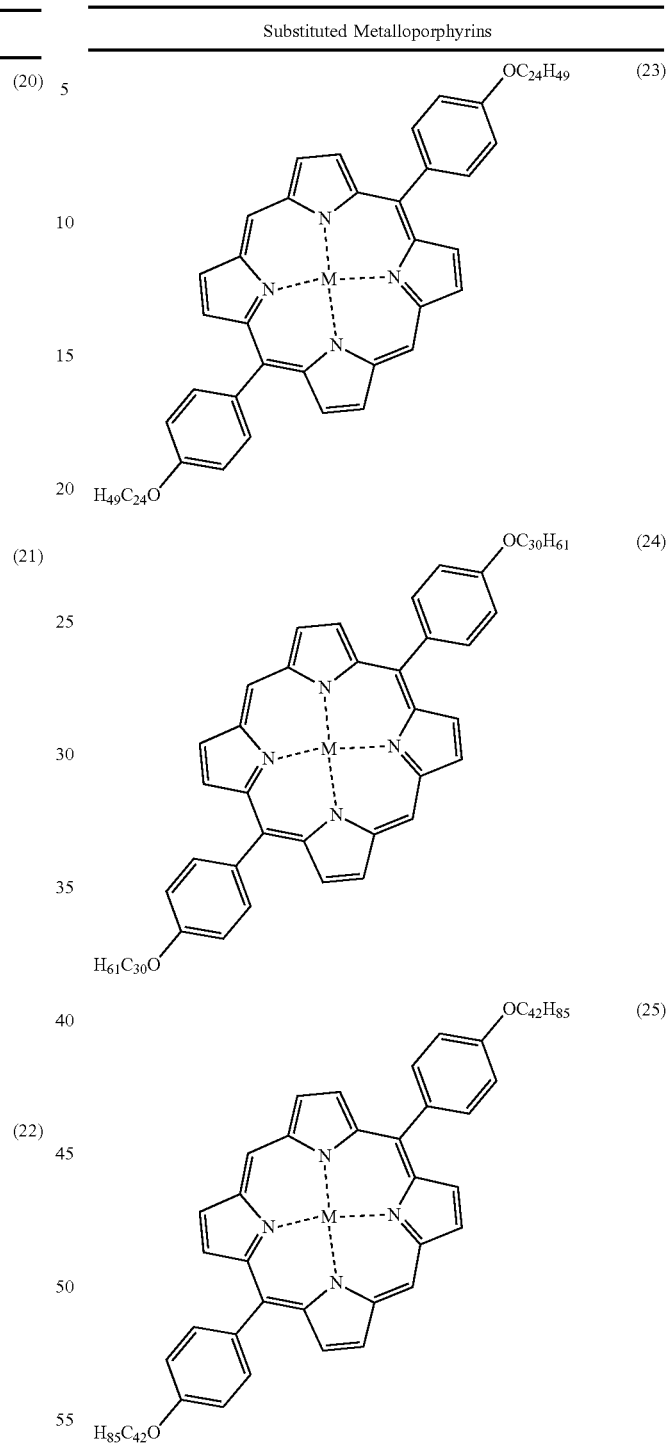

(23), (24), (25)

In the embodiments shown in formulas (20) through (25), M is a metal including but not limited to aluminum, calcium, magnesium, manganese, iron, cobalt, nickel, zinc, ruthenium, palladium, silver, platinum, indium, tin, copper, rhodium, chromium, gallium, osmium, iridium, or derivatives thereof; and where the oxidation state of the metal can include, but not be limited to an oxidation state of I, II, III, IV, V, VI, VII, or VIII. In some embodiments, the metal is magnesium. In some embodiments the metal is silver. In some embodiments the metal is platinum. In some embodiments the metal is palladium. In some embodiments the metal is zinc. In some embodiments, various inorganic, organic, ionic, or neutral ligands can be coordinated with the metals herein, including, but not to be limited to, $Cl^-$, $F^-$, $Br^-$, $I^-$, $CN^-$, $SCN^-$, CO, $NH_3$, $H_2O$, NO, $CH_3NH_2$, pyridine, and the like. In some embodiments, the number of ligands can be from zero ligands to eight ligands.

In some embodiments, the substituted metalloporphyrins can include those including phthalocyanine substitutions in the place of one or more of the pyrrole subunits of the metalloporphyrin ring structure of formula (17). The phthalocyanine-substituted metalloporphyrins include those having the general formulas (26) through (30), as shown in TABLE 5.

TABLE 5

Phthalocyanine-substituted metalloporphyrins

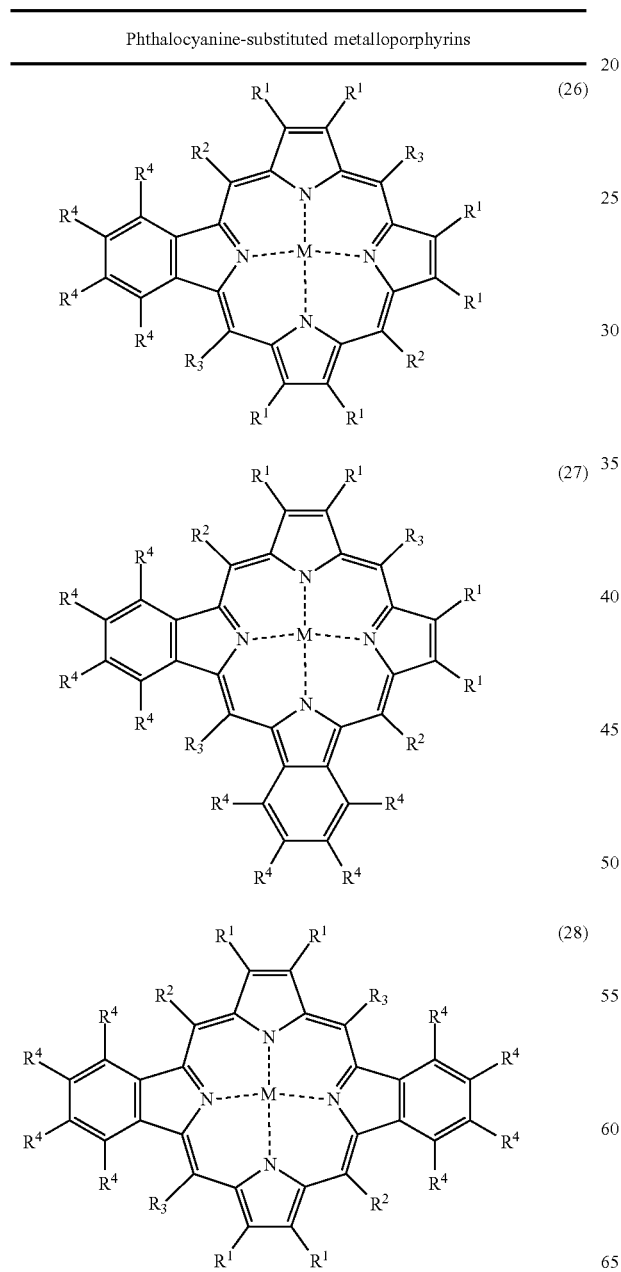

TABLE 5-continued

Phthalocyanine-substituted metalloporphyrins

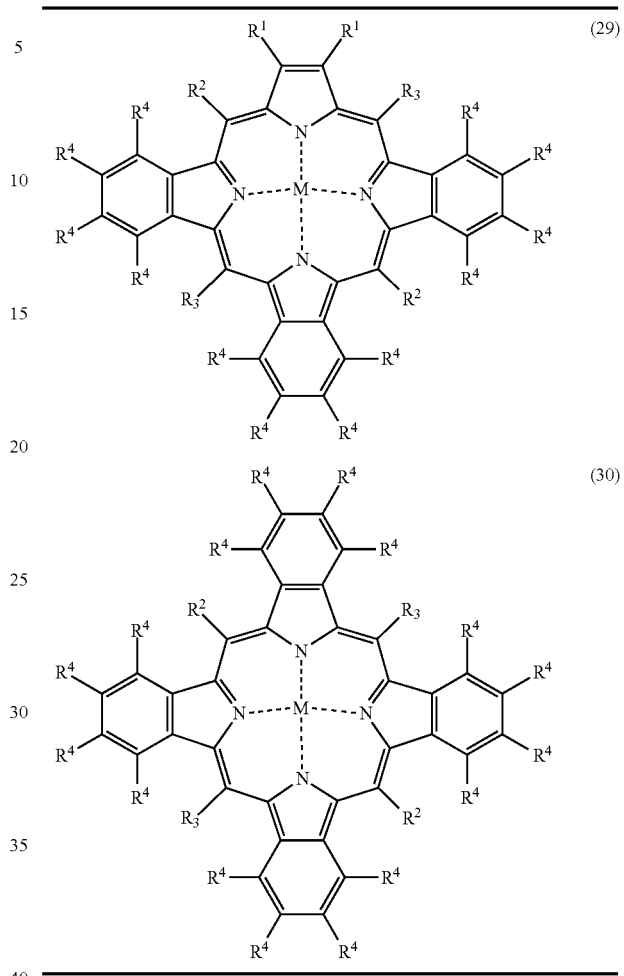

where each $R^1$ and $R^4$ are independently —H; —X, where X is a halogen atom; any linear or branched $C_1$-$C_{50}$ alkyl, $C_1$-$C_{50}$ alkenyl, $C_1$-$C_{50}$ alkynyl, $C_1$-$C_{50}$ heteroalkyl, $C_1$-$C_{50}$ heteroalkenyl, $C_1$-$C_{50}$ heteroalkynyl, or any combination thereof; —RZR, —ZRZR, or —RZRZR, where R can include, but not be limited to, any identical or different, linear or branched, $C_1$-$C_{50}$ alkyl, $C_1$-$C_{50}$ alkenyl, $C_1$-$C_{50}$ alkynyl, or any combination thereof, and Z can be one or more heteroatom selected from N, O, P, S, Se, or Si; —ROH, —RC(O)OH, —RC(O)OR, —ROR, —RSR, —RCHO, —RX, —RC(O)$NH_2$, —RC(O)NR, —$RNH_3^+$, —$RNH_2$, —$RNO_2$, —RNR, —RNRR, —$RB(OH)_2$, or any combination thereof, where R can include, but is not to be limited to, any identical or different, linear, branched, or cyclic $C_1$-$C_{50}$ alkyl, $C_1$-$C_{50}$ alkenyl, $C_1$-$C_{50}$ alkynyl, or a combination thereof, or can be absent such that the remaining portion of the functional group is covalently bound directly to one or more carbon atoms of the phthalocyanine-substituted metalloporphyrin; and where $R^2$ and $R^3$ are independently —H; any linear or branched $C_1$-$C_{50}$ alkyl, $C_1$-$C_{50}$ alkenyl, $C_1$-$C_{50}$ alkynyl, $C_1$-$C_{50}$ heteroalkyl, $C_1$-$C_{50}$ heteroalkenyl, $C_1$-$C_{50}$ heteroalkynyl, or any combination thereof; —RZR, —ZRZR, or —RZRZR, where R can include, but not be limited to, any identical or different, linear or branched, $C_1$-$C_{50}$ alkyl, $C_1$-$C_{50}$ alkenyl, $C_1$-$C_{50}$ alkynyl, or any combination thereof, and Z can be one or more heteroatom selected from N, O, P, S, Se, or Si; an aryl, heteroaryl, substituted aryl, or substituted heteroaryl; a biphenyl or substituted biphenyl; an aryloxy, arylthio, arylamine, or any substitutions thereof; or any combination thereof; and where every $R^1$, $R^2$, $R^3$, and $R^4$ group is covalently bound directly to the phthalocyanine-substituted metalloporphyrin; and where M is a metal including but not limited to aluminum, calcium, magnesium, manganese, iron, cobalt, nickel, zinc, ruthenium, palladium, silver, platinum, indium, tin, copper, rhodium, chromium, gallium, osmium, iridium, or derivatives thereof; and where the oxidation state of the metal can include, but not be limited to an oxidation state of I, II, III, IV, V, VI, VII, or VIII. In some embodiments, the metal is magnesium. In some embodiments the metal is silver. In some embodiments the metal is platinum. In some embodiments the metal is palladium. In some embodiments the metal is zinc. In some embodiments, various inorganic, organic, ionic, or neutral ligands can be coordinated with the metals herein, including, but not to be limited to, $Cl^-$, $F^-$, $Br^-$, $I^-$, $CN^-$, $SCN^-$, $CO$, $NH_3$, $H_2O$, $NO$, $CH_3NH_2$, pyridine, and the like. In some embodiments, the number of ligands can be from zero ligands to eight ligands.

In some embodiments, the $R^2$ and $R^3$ groups are the same, while in other embodiments the $R^2$ and $R^3$ groups are different.

In some embodiments, the substituted metalloporphyrins herein can include one or more expanded substituted metalloporphyrins. As used herein, the term "expanded substituted metalloporphyrin" refers to a metalloporphyrin having an expanded ring structure including more than the four pyrrole rings associated with the structure shown in formula (11). In some embodiments, the expanded substituted metalloporphyrin can include 5 modified pyrrole subunits, each connected by a methine (=CH—) bridge. In some embodiments, the expanded substituted metalloporphyrin ring structure can include 6 modified pyrrole subunits, each connected by a methine (=CH—) bridge. In some embodiments, the expanded substituted metalloporphyrin ring structure can include more than 6 modified pyrrole subunits, each connected by a methine (=CH—) bridge. Exemplary expanded substituted metalloporphyrin molecules include, but are not to be limited to, those expanded substituted metalloporphyrin molecules having the general formulas (9) and (10) as shown in TABLE 6.

TABLE 6

Expanded Substituted Metalloporphyrins

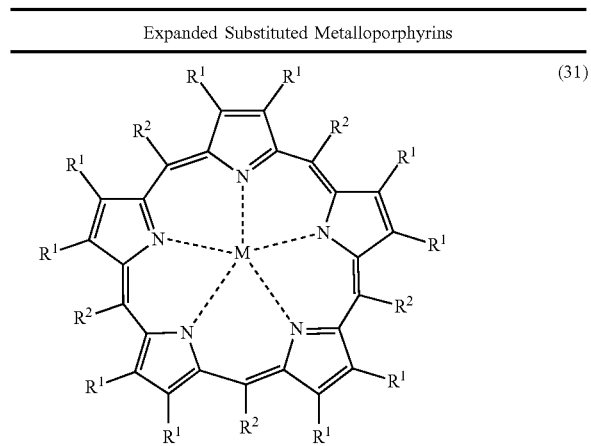

(31)

TABLE 6-continued

Expanded Substituted Metalloporphyrins

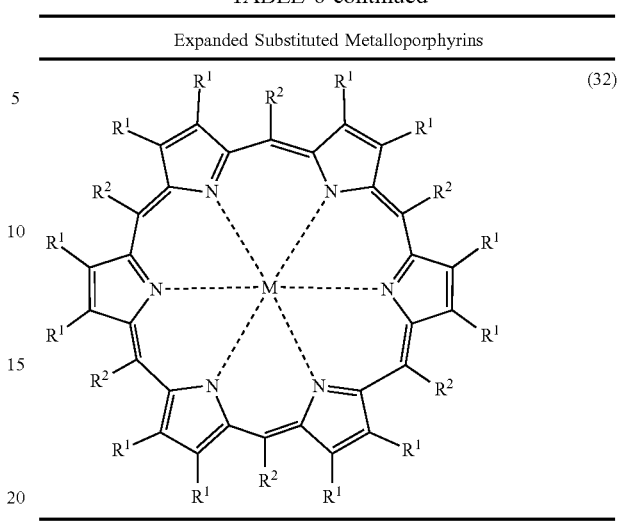

(32)

where each $R^1$ is independently —H; —X, where X is a halogen atom; any linear or branched $C_1$-$C_{50}$ alkyl, $C_1$-$C_{50}$ alkenyl, $C_1$-$C_{50}$ alkynyl, $C_1$-$C_{50}$ heteroalkyl, $C_1$-$C_{50}$ heteroalkenyl, $C_1$-$C_{50}$ heteroalkynyl, or any combination thereof; —RZR, —ZRZR, or —RZRZR, where R can include, but not be limited to, any identical or different, linear or branched, $C_1$-$C_{50}$ alkyl, $C_1$-$C_{50}$ alkenyl, $C_1$-$C_{50}$ alkynyl, or a combination thereof, and Z can be one or more heteroatom selected from N, O, P, S, Se, or Si; —ROH, —RC(O)OH, —RC(O)OR, —ROR, —RSR, —RCHO, —RX, —RC(O)NH$_2$, —RC(O)NR, —RNH$_3^+$, —RNH$_2$, —RNO$_2$, —RNR, —RNRR, —RB(OH)$_2$, or any combination thereof, where R can include, but is not to be limited to, any identical or different, linear, branched, or cyclic $C_1$-$C_5$ alkyl, $C_1$-$C_{50}$ alkenyl, $C_1$-$C_{50}$ alkynyl, or a combination thereof, or can be absent such that the remaining portion of the functional group is covalently bound directly to one or more carbon atoms of the expanded substituted metalloporphyrin; and where $R^2$ is independently —H; any linear or branched $C_1$-$C_{50}$ alkyl, $C_1$-$C_{50}$ alkenyl, $C_1$-$C_{50}$ alkynyl, $C_1$-$C_{50}$ heteroalkyl, $C_1$-$C_{50}$ heteroalkenyl, $C_1$-$C_{50}$ heteroalkynyl or any combination thereof; —RZR, —ZRZR, or —RZRZR, where R can include, but not be limited to, any identical or different, linear or branched, $C_1$-$C_{50}$ alkyl, $C_1$-$C_{50}$ alkenyl, $C_1$-$C_{50}$ alkynyl, or any combination thereof, and Z can be one or more heteroatom selected from N, O, P, S, Se, or Si; an aryl, heteroaryl, substituted aryl, or substituted heteroaryl; a biphenyl or substituted biphenyl; an aryloxy, arylthio, arylamine, or any substitutions thereof; or any combination thereof; and where every $R^1$ and $R^2$ group is covalently bound directly to the expanded substituted metalloporphyrin; and where M is a metal including but not limited to aluminum, calcium, magnesium, manganese, iron, cobalt, nickel, zinc, ruthenium, palladium, silver, platinum, indium, tin, copper, rhodium, chromium, gallium, osmium, iridium, or derivatives thereof; and where the oxidation state of the metal can include, but not be limited to an oxidation state of I, II, III, IV, V, VI, VII, or VIII. In some embodiments, the metal is magnesium. In some embodiments the metal is silver. In some embodiments the metal is platinum. In some embodiments the metal is palladium. In some embodiments the metal is zinc. In some embodiments, various inorganic, organic, ionic, or neutral ligands can be coordinated with the metals herein, including, but not to be limited to, $Cl^-$, $F^-$, $Br^-$, $I^-$, $CN^-$, $SCN^-$, $CO$, $NH_3$, $H_2O$, $NO$, $CH_3NH_2$, pyridine, and the like. In some embodiments, the number of ligands can be from zero ligands to eight ligands.

It will be appreciated that the expanded substituted metalloporphyrin ring structures described herein can further include those having phthalocyanine substitutions in the place of one or more of the pyrrole subunits of the porphyrin ring structures of formulas (31) and (32).

The self-assembled monolayers can include those that are homogeneous and those that are heterogeneous (e.g., they can include a layer having a mixture of more than one type of substituted porphyrin and/or substituted metalloporphyrin). In some embodiments a self-assembled monolayer can be monofunctional and in other embodiments a self-assembled monolayer can be bifunctional, trifunctional, etc. In some embodiments, the self-assembled monolayer can include at least about 5%, 10%, 15%, 20%, 25%, 30%, 40%, or 50% of a secondary compound (or an amount falling within a range between any of these amounts), which can be any of the compounds described herein, but different than a primary compound which accounts for the substantial balance of the coverage of the graphene layer.

In some embodiments, the graphene layer can be disposed on the surface of a substrate. Substrate materials suitable for use herein can include metals such as copper, nickel, ruthenium, platinum, iridium, and the like, and metal oxides such as copper oxide, zinc oxide, magnesium oxide, and the like. Substrate materials can also include silicon, quartz, sapphire, glass, ceramic, polymers, etc.

Further aspects of exemplary graphene varactors can be found in U.S. Pat. No. 9,513,244, the content of which is herein incorporated by reference in its entirety.

Contact Angle Goniometry

Contact angle goniometry can be used to determine the wettability of a solid surface by a liquid. Wettability, or wetting, can result from the intermolecular forces at the contact area between a liquid and a solid surface. The degree of wetting can be described by the value of the contact angle $\Phi$ formed between the area of contact between the liquid and the solid surface and a line tangent to the liquid-vapor interface. When a surface of a solid is hydrophilic and water is used as the test liquid, (i.e., a high degree of wettability), the value for $\Phi$ can fall within a range of 0 to 90 degrees. When a surface of a solid is moderately hydrophilic to hydrophobic, (i.e., a medium degree of wettability), the value for $\Phi$ for water as the test liquid can fall within a range of 85 to 105 degrees. When the surface of a solid is highly hydrophobic, (i.e., a low degree of wettability), the value for $\Phi$ with water as the test liquid can fall within a range of 90 to 180 degrees. Thus, a change in contact angle can be reflective of a change in the surface chemistry of a substrate.

Graphene surfaces and modifications made to graphene surfaces can be characterized using contact angle goniometry. Contact angle goniometry can provide quantitative information regarding the degree of modification of the graphene surface. Contact angle measurements are highly sensitive to the functional groups present on sample surfaces and can be used to determine the formation and extent of surface coverage of self-assembled monolayers. A change in the contact angle from a bare graphene surface as compared to one that has been immersed into a self-assembly solution containing π-electron-rich molecules, can be used to confirm the formation of the self-assembled monolayer on the surface of the graphene.

The types of solvents suitable for use in determining contact angle measurements, also called wetting solutions, are those that maximize the difference between the contact angle of the solution on bare graphene and the contact angle on the modified graphene, thereby improving data accuracy for measurements of binding isotherms. In some embodiments, the wetting solutions can include, but are not limited to, deionized (DI) water, NaOH aqueous solution, borate buffer (pH 9.0), other pH buffers, $CF_3CH_2OH$, and the like. In some embodiments, the wetting solutions are polar. In some embodiments, the wetting solutions are non-polar.

Langmuir Adsorption Theory

Without wishing to be bound by any particular theory, it is believed that according to Langmuir adsorption theory, monolayer modification of graphene can be controlled by varying the concentration of the adsorbate in the bulk of the self-assembly solution according to:

$$\theta = \frac{K*C}{1+K*C} \quad (1)$$

where $\theta$ is the fractional surface coverage, C is the concentration of the adsorbate in the bulk of the self-assembly solution, and K is the equilibrium constant for adsorption of the adsorbate to graphene. Experimentally, the surface coverage can be expressed by the change in contact angle between bare graphene and modified graphene according to:

$$\theta = \frac{\Phi(i) - \Phi(\text{bare})}{\Phi(sat.) - \Phi(\text{bare})} \quad (2)$$

where $\Phi(i)$ is the contact angle of the modified graphene as a function of the concentration in the self-assembly solution, $\Phi(\text{bare})$ is the contact angle of bare graphene, and $\Phi(sat.)$ is the contact angle of graphene modified with a complete monolayer of receptor molecules (i.e., 100% surface coverage or $\theta=1.0$). Insertion of $\theta$ from eq. (2) into eq. (1) and solving for $\Phi(i)$ gives eq. (3)

$$\Phi(i) = \Phi(\text{bare}) + \frac{K*C[\Phi(sat.) - \Phi(\text{bare})]}{1+K*C} \quad (3)$$

Thus, the experimentally observed $\Phi(i)$ values can be fitted as a function of receptor concentration in the self-assembly solution, using the two fitting parameters K and $\Phi(sat.)$. Once these two parameters have been determined, relative surface coverages at different self-assembly concentrations can be predicted from eq. (1), using K.

Data can be fitted with the Langmuir adsorption model to determine the equilibrium constants for surface adsorption and the concentrations of self-assembly solutions needed to form dense monolayers having 90% or greater surface coverage (i.e., $\theta>0.9$) on graphene. In some embodiments, a surface coverage of at least 90% or greater is desired. In some embodiments, a surface coverage of at least 95% or greater is desired. In some embodiments, a surface coverage of at least 98% or greater is desired.

Figure 10:
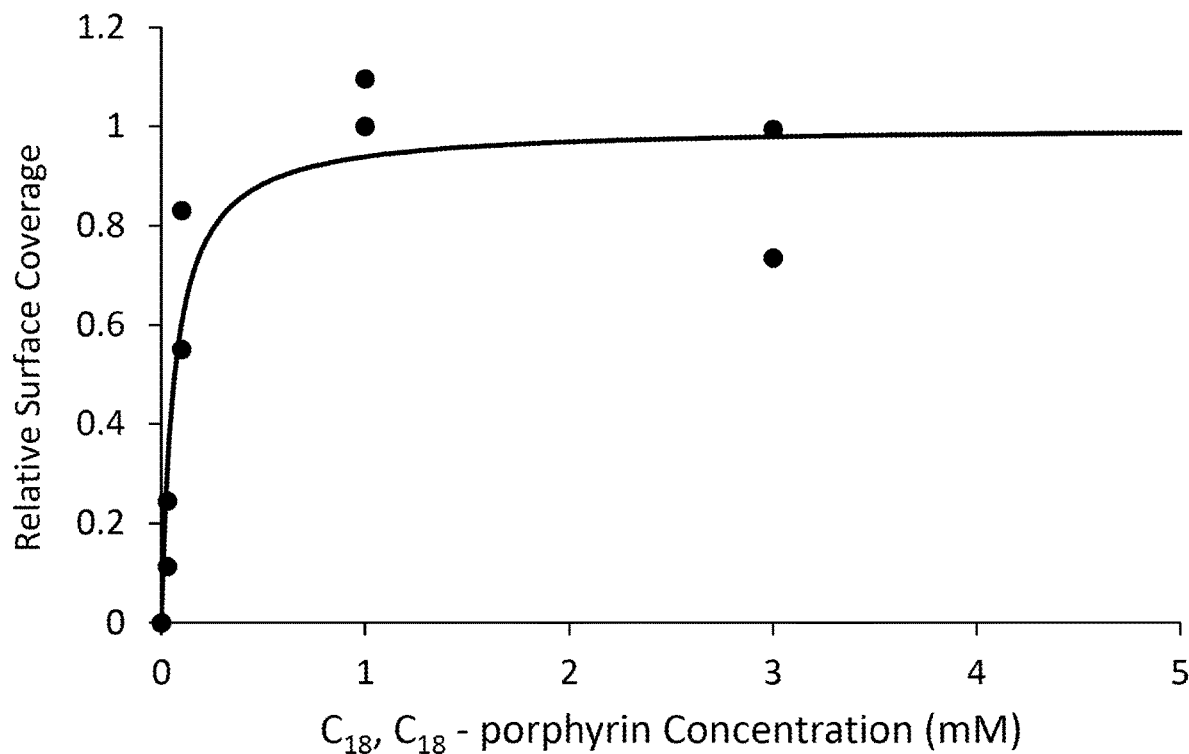
FIG. 10 is a representative plot of relative surface coverage as a function of concentration in accordance with various embodiments herein.
Figure 11:
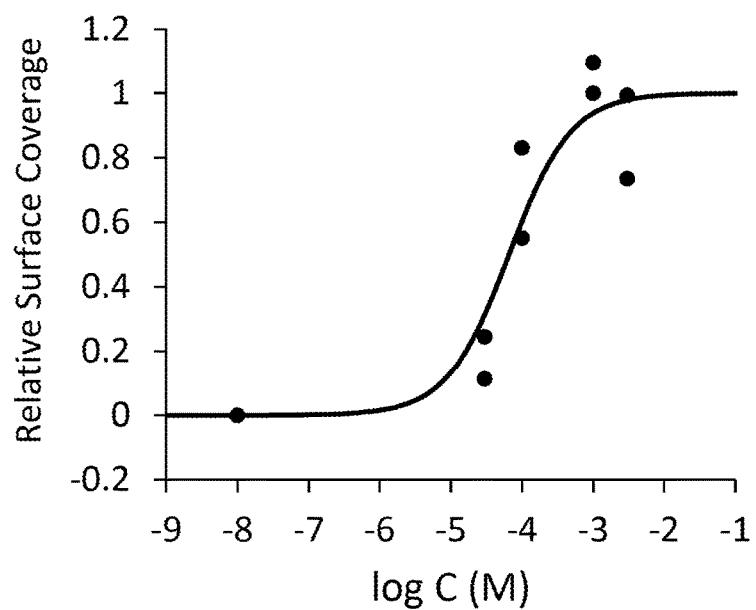
FIG. 11 is a representative plot of relative surface coverage as a function of the logarithm of concentration presented in FIG. 10, in accordance with various embodiments herein.

A representative Langmuir adsorption isotherm for the adsorption of a substituted porphyrin to graphene is shown in FIG. 10 and described more fully in Example 4 below. The data show the relative monolayer coverage (dots) along with a fit based on Langmuir adsorption theory (solid line) for the adsorption of 5,15-bis(4-octadecyloxyphenyl)-porphyrin (herein "$C_{18},C_{18}$-porphyrin") to graphene, as determined by XPS measurements. The logarithm of the concentration as a function of relative surface coverage for the adsorption of $C_{18},C_{18}$-porphyrin to graphene is shown in FIG. 11.

In the above example, the Langmuir model is used to determine K from the elemental compositions of the bare graphene and modified graphene surfaces obtained using X-ray photoelectron spectroscopy (XPS). Instead of using XPS data, data obtained with infrared spectroscopy or Raman spectroscopy, or contact angle goniometry can also be used.

X-Ray Photoelectron Spectroscopy

X-ray photoelectron spectroscopy (XPS) is a highly sensitive spectroscopic technique that can quantitatively measure the elemental composition of a surface of a material. The process of XPS involves irradiation of a surface with X-rays under a vacuum, while measuring the kinetic energy and electron release within the top 0 to 10 nm of a material. Without wishing to be bound by any particular theory, it is believed that XPS can be used to confirm the presence of a self-assembled monolayer formed on the surface of graphene.

The surface concentrations of the types of atoms that the monolayer, graphene, and the underlying substrate consist of (as determined from XPS) depends on the Langmuir theta value of the monolayer or, in other words, the surface density of the monolayer molecules on the graphene. For example, the surface concentrations of carbon, oxygen, and copper (i.e., C %, O %, and Cu %, as determined from XPS) for the monolayers of any given cyclodextrin on a copper substrate depends on the concentration of that cyclodextrin in the self-assembly solution. Due to experimental error, a slightly different value of the equilibrium constant, K, for surface adsorption will result when either the C %, O %, or Cu % data are fitted separately. However, because the C %, O %, or Cu % data characterize the same equilibrium, there is only one true value for K. Therefore, the XPS data can not only be fitted separately for the C %, O %, and Cu % data but also as one combined set of data. Fitting of the combined data for several types of atoms that the monolayer, graphene, and the underlying substrate consist of gives more accurate estimates of the true value of K. For this purpose, the following equation can be used, where each data point consists of a vector comprising (i) an index, (ii) the concentration of the self-assembly solution, and (iii) the carbon, oxygen, or copper concentration as determined by XPS.

$$KroneckerDelta[1 - \text{index}] *$$
$$\left\{ C\ \%(\text{bare}) + \frac{K * Conc * [C\ \%(sat.) - C\ \%(\text{bare})]}{1 + K * Conc} \right\} +$$
$$KroneckerDelta[2 - \text{index}] *$$
$$\left\{ O\ \%(\text{bare}) + \frac{K * Conc * [O\ \%(sat.) - O\ \%(\text{bare})]}{1 + K * Conc} \right\} +$$
$$KroneckerDelta[3 - \text{index}] *$$
$$\left\{ Cu\ \%(\text{bare}) + \frac{K * Conc * [Cu\ \%(sat.) - Cu\ \%(\text{bare})]}{1 + K * Conc} \right\}$$

The index 1 was used for the C % data, 2 for the 0% data, and 3 for the Cu % data. The output of the Kronecker delta for the input of 0 is 1, and it is 0 for any other input. This fitting procedure provides in one step the maximum surface concentrations of carbon, oxygen, and copper (i.e., C % (sat.), O % (sat.), and Cu % (sat.), respectively) along with one single value for K for all three adsorption isotherms.

In the example above, the K value is fitted from 3 adsorption isotherms, that is, the surface concentrations of 3 types of atoms. The same type of fit may also be performed for adsorption isotherms of 1, 2, 3, 4, 5, 6, 7, 8, 9, 10, or more different types of atoms.

The equilibrium constant K, as determined by the fit of the XPS data, can be used in the Langmuir adsorption model to determine the 0 value for graphene surfaces modified with various molecules forming monolayers on graphene, such as substituted porphyrins, substituted metalloporphyrins, and their derivatives. A representative Langmuir adsorption isotherm for the adsorption of graphene modified with $C_{18}$, $C_{18}$-porphyrin is shown in FIG. 10 and described in more detail in Example 4.

Aspects may be better understood with reference to the following examples. These examples are intended to be representative of specific embodiments, but are not intended as limiting the overall scope of embodiments herein.

EXAMPLES

Example 1: Synthesis of 5,15-bis(4-octadecyloxyphenyl)-porphyrin

Figure 9:
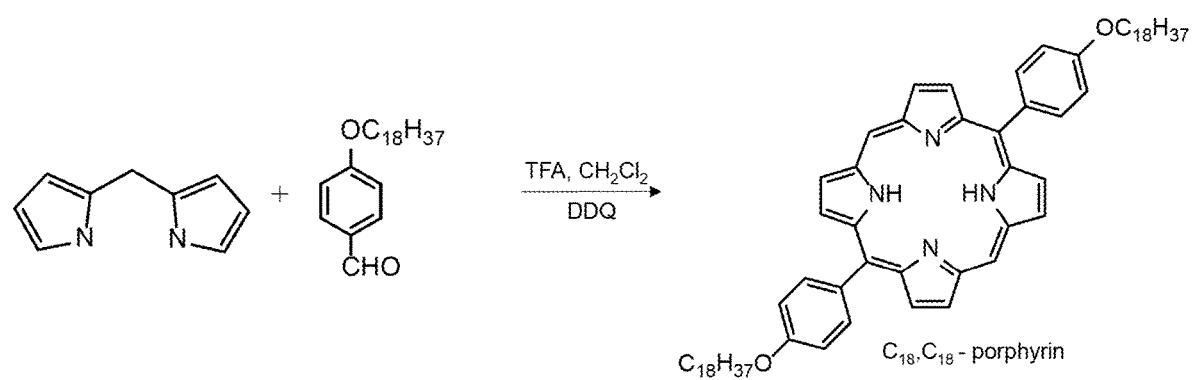
FIG. 9 is a reaction pathway for the synthesis of porphyrin derivatives in accordance with various embodiments herein.

The substituted 5,15-bis(4-octadecyloxyphenyl)-porphyrin (herein "$C_{18},C_{18}$-porphyrin") was synthesized according to the reaction scheme shown in FIG. 9.

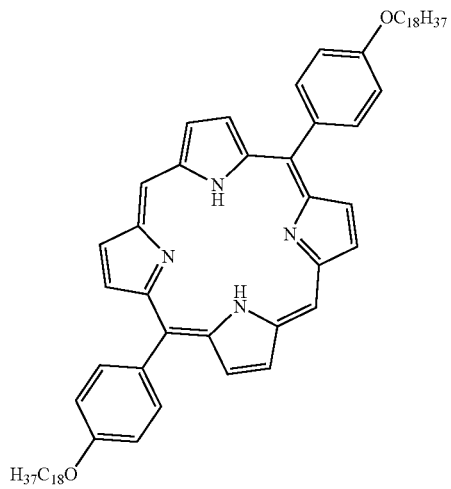

Briefly, 150.0 mg of 2,2'-dipyrrolmethane and 384.4 mg of 4-octadecyloxybenzaldehyde were added to a 250 mL 2-neck round bottom flask, and the flask was vacuumed and refilled with $N_2$ gas three times. 100 mL of anhydrous dichloromethane ($CH_2Cl_2$) was degassed with $N_2$ for 15 min and then transferred to the round bottom flask. 50 μL of trifluoroacetic acid (TFA) was then added to the round bottom flask using a syringe, and the mixture was stirred at room temperature in the dark for 15 h under $N_2$ protection. After incubation overnight, 515.2 mg of 2,3-dichloro-5,6-dicyano-1,4-benzoquinone (DDQ) was added to the mixture, and the reaction was left to proceed for 3 h. The reaction was stopped by the addition of 2 mL of triethylamine. The product solution was passed through an alumina column, and solvents were allowed to evaporate. The remaining solid product was purified via chromatography on silica using $CH_2Cl_2$ as the eluent ($R_f$=1), followed by recrystallization in MeOH/$CH_2Cl_2$, giving a purple solid. The following $^1$H NMR (δ, ppm, CD$_2$Cl$_2$) results were obtained: 10.38 (s, 2H, —C═H), 9.48 (d, 4H, aromatic H), 9.18 (d, 4H, aromatic H), 8.23 (d, 4H, aromatic H), 7.41 (d, 4H, aromatic H), 4.33 (t, 4H, —OCH$_2$—), 2.06 (tt, 4H, —CH$_2$—), 1.69 (tt, 4H, —CH$_2$—), 1.30 (m, 56H, —CH$_2$—), 0.91 (t, 6H, —CH$_3$), −3.08 (s, 2H, —NH—). Mass spectrometry (MALDI, 25 mM 2,5-dihydroxybenzoic acid as matrix) results were: m/z: 999.6 (C$_{18}$,C$_{18}$-porphyrin•H$^+$). Elemental analysis of the solid was as follows: calculated C, 81.71%; H, 9.48%; N, 5.61%; observed C, 81.86%; H, 9.55%; N, 5.63%.

Example 2: Graphene Surface Modification with C$_{18}$,C$_{18}$-porphyrin

Graphene substrates were immersed overnight into self-assembly solutions containing chlorobenzene and the C$_{18}$,C$_{18}$-porphyrin construct (See Example 1) at various concentrations (0, 0.03, 0.10, 1.0, or 3.0 mM) using chlorobenzene as the solvent. The modified graphene substrates were washed 3 times with small portions of chlorobenzene to remove excess self-assembly solution.

Suitable graphene substrates for use in creating self-assembled monolayers include monolayer graphene on Cu foil as purchased from Graphenea (Donostia, Spain) and monolayer graphene as grown on 25-μm-thick Cu foils (No. 46365, Alfa Aesar, Tewksbury, Mass.) by chemical vapor deposition using hydrogen and methane flow rates of 21 standard cubic centimeter per minute (sccm) and 0.105 sccm, respectively, at 1050° C.

Example 3: XPS of Bare Graphene

X-ray photoelectron spectroscopy (XPS) spectra of bare graphene on a copper substrate were collected on a VersaProbe III Scanning XPS Microprobe (PHI 5000, Physical Electronics, Chanhassen, Minn.). The observed elemental surface composition of bare graphene on a copper substrate was found to be 57.1 mol % carbon, 12.7 mol % oxygen, and 30.2 mol % copper, as shown in TABLE 7.

Example 4: XPS of Graphene Modified with C$_{18}$,C$_{18}$-porphyrin

XPS of graphene modified with C$_{18}$,C$_{18}$-porphyrin was performed to determine the Carbon % (C %), Oxygen % (O %), and Copper % (Cu %) of the modified surface. The XPS spectra were collected on a VersaProbe III Scanning XPS Microprobe (PHI 5000, Physical Electronics, Chanhassen, Minn.).

The results for the elemental surface composition of graphene modified with C$_{18}$,C$_{18}$-porphyrin are shown in TABLE 7. The Langmuir adsorption isotherm for the adsorption of graphene modified with C$_{18}$,C$_{18}$-porphyrin is shown in FIG. 10. The data show the relative monolayer coverage (dots) along with a fit (solid line) based on Langmuir adsorption theory for the adsorption of graphene modified with C$_{18}$,C$_{18}$-porphyrin, as determined by XPS data. The relative surface coverage for the adsorption of C$_{18}$,C$_{18}$-porphyrin to graphene as a function of the logarithm of the C$_{18}$,C$_{18}$-porphyrin concentration in the self-assembly solution is shown in FIG. 11.

TABLE 7

Elemental surface composition of graphene modified with C$_{18}$,C$_{18}$-porphyrin, as determined by XPS

| C$_{18}$,C$_{18}$-porphyrin Concentration (mM) in self-assembly solution | C % | Cu % | O % |
|---|---|---|---|
| 0 | 57.1 ± 1.4 | 30.2 ± 2.7 | 12.7 ± 1.4 |
| 0.03 | 58.3 ± 0.6 | 29.5 ± 2.0 | 12.2 ± 2.2 |
| 0.10 | 59.8 ± 1.7 | 25.3 ± 2.8 | 14.8 ± 1.1 |
| 1.0 | 62.0 ± 0.7 | 23.7 ± 1.7 | 14.2 ± 1.2 |
| 3.0 | 62.0 ± 0.5 | 25.9 ± 1.0 | 12.2 ± 0.6 |

The C % and Cu % data were fitted simultaneously, as described above, to determine the equilibrium constant K. The O % data were not included into the fitting because the maximum change in O % fell within the background noise of the experiment. The equilibrium constant, K, and concentration of self-assembly solution needed for at least 90% monolayer formation with C$_{18}$,C$_{18}$-porphyrin are shown in TABLE 8.

TABLE 8

Equilibrium constants and monolayer concentrations for adsorption of C$_{18}$,C$_{18}$-porphyrin on graphene

| Self-Assembly Molecule | Log K (Log M$^{-1}$) | Self-assembly solvent | Concentration of self-assembly solution needed for 90% surface coverage (mM) |
|---|---|---|---|
| C$_{18}$,C$_{18}$-porphyrin | 4.18 (3.90-4.35) | chlorobenzene | 0.6 |

Figure 12:
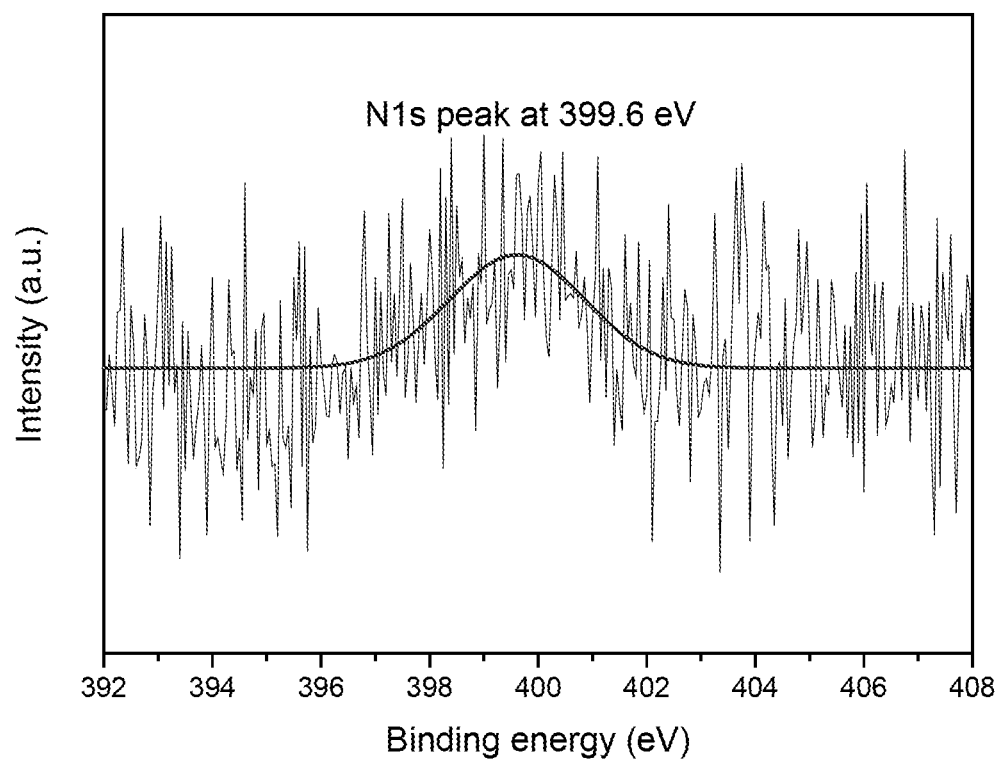
FIG. 12 is a representative high-resolution XPS spectrum and fits in accordance with various embodiments herein.
Figure 13:
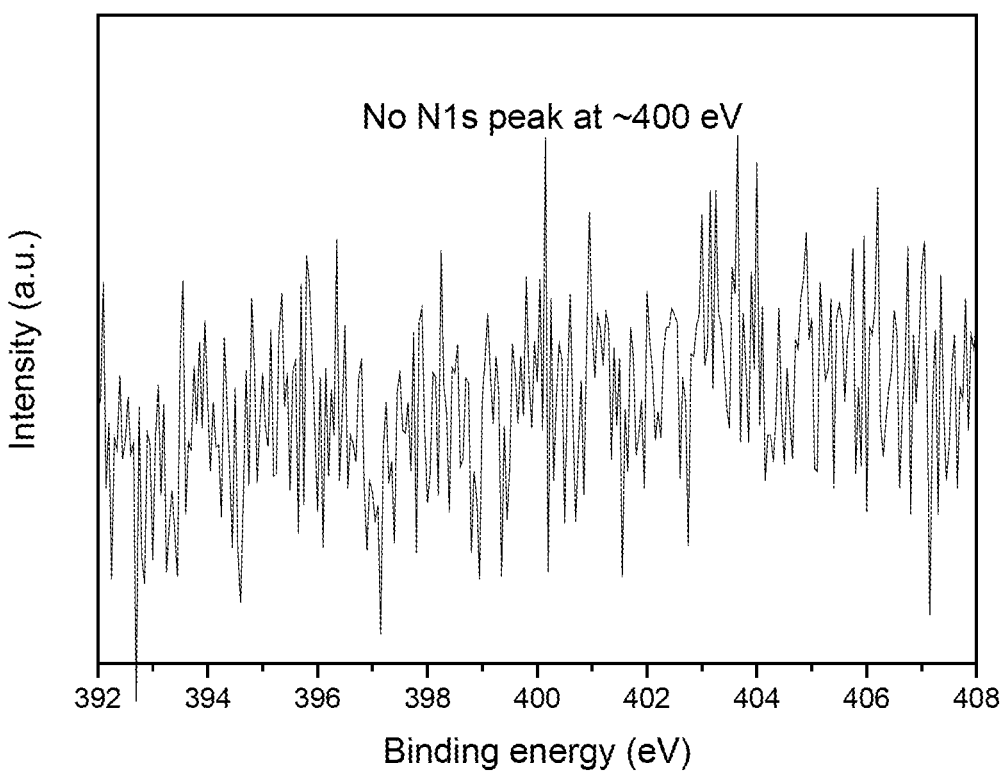
FIG. 13 is a representative high-resolution XPS spectrum in accordance with various embodiments herein.

Further, modification of graphene with C$_{18}$,C$_{18}$-porphyrin can be confirmed by the presence of nitrogen in the N1s XPS spectrum. The N1s XPS spectrum for graphene modified with C$_{18}$,C$_{18}$-porphyrin reveals an N1s peak at approximately 399.6 eV (FIG. 12). In contrast, the N1s XPS spectrum for bare graphene reveals no peaks for nitrogen at or near approximately 400 eV (FIG. 13).

Example 5: Synthesis of Zn(II) 5,15-bis(4-octadecyloxyphenyl)porphyrin

The substituted Zn(II) 5,15-bis(4-octadecyloxyphenyl)porphyrin (herein "Zn(II) C$_{18}$,C$_{18}$—Zn(II)porphyrin") was synthesized.

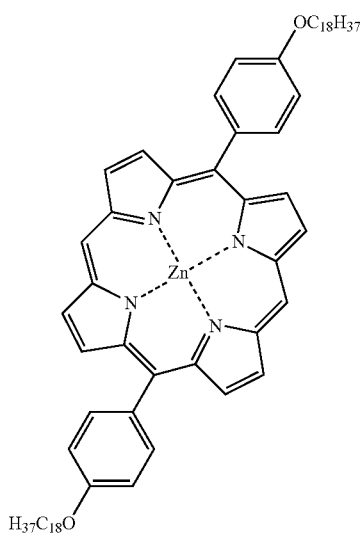

Briefly, 32.0 mg of $C_{18},C_{18}$-porphyrin and 70.3 mg of Zn(II) acetate dihydrate were dissolved in 5 mL anhydrous dimethyl formamide and the mixture was refluxed for 24 h under the protection of $N_2$. After the 24 hr incubation period, 10 mL of water was added to the mixture to form a precipitate. The precipitate was collected, washed with water, and recrystallized in $CH_2Cl_2$. The following $^1H$ NMR (δ, ppm, $CD_2Cl_2$) results were obtained: 10.40 (s, 2H, —C═H), 9.53 (d, 4H, aromatic H), 9.24 (d, 4H, aromatic H), 8.22 (d, 4H, aromatic H), 7.39 (d, 4H, aromatic H), 4.34 (t, 4H, —$OCH_2$—), 2.05 (tt, 4H, —$CH_2$—), 1.67 (tt, 4H, —$CH_2$—), 1.30 (m, 56H, —$CH_2$—), 0.92 (t, 6H, —$CH_3$). Mass spectrometry (MALDI, 25 mM 2,5-dihydroxybenzoic acid as matrix) results were: m/z: 1060.6 (Zn(II) $C_{18},C_{18}$-porphyrin•$H^+$).

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A medical device comprising:
   a chemical sensor element comprising a plurality of graphene varactors;
   at least one of the plurality of graphene varactors comprising:
   a graphene layer;
   a self-assembled monolayer disposed on an outer surface of the graphene layer through electrostatic interactions between a partial positive charge on hydrogen atoms of one or more hydrocarbons of the self-assembled monolayer and a π-electron system of graphene; and
   wherein the self-assembled monolayer comprises substituted porphyrins of the formula (I):

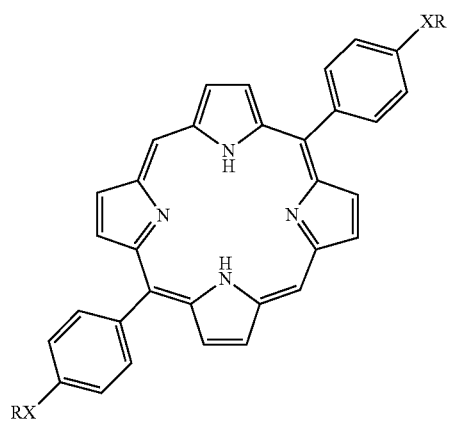

wherein each X is independently a heteroatom comprising N, O, P, S, Se, or Si, or absent, such that R is covalently attached to the phenyl group; and wherein each R functional group independently comprises: —H; any linear or branched $C_i$-$C_{50}$ alkyl, $C_1$-$C_{50}$ alkenyl, $C_1$-$C_{50}$ alkynyl, $C_1$-$C_{50}$ heteroalkyl, $C_1$-$C_{50}$ heteroalkenyl, $C_1$-$C_{50}$ heteroalkynyl, or any combination thereof, —RZR, —ZRZR, or —RZRZR, wherein R comprises any identical or different, linear or branched, $C_1$-$C_{50}$ alkyl, $C_1$-$C_{50}$ alkenyl, $C_1$-$C_{50}$ alkynyl, or any combination thereof, and Z can be one or more heteroatom selected from N, O, P, S, Se, or Si; an aryl, heteroaryl, substituted aryl, or substituted heteroaryl; a biphenyl or substituted biphenyl; an aryloxy, arylthio, arylamine, or any substitutions thereof, or any combination thereof.

2. The medical device of claim 1, wherein the self-assembled monolayer provides a Langmuir theta value of at least 0.9.

3. The medical device of claim 1, wherein the self-assembled monolayer provides a Langmuir theta value of at least 0.98.

4. The medical device of claim 1, wherein the self-assembled monolayer includes a multilayer that provide coverage over the graphene from 50% to 150% by surface area.

5. The medical device of claim 1, comprising the plurality of graphene varactors configured in an array on the medical device.

6. A method for detecting an analyte using the medical device of claim 1 comprising the steps of:
  collecting a gaseous sample from a patient;
  the gaseous sample contacting the at least one of the plurality of graphene varactors, each of the one or more graphene varactors.

7. The method of claim 6, further comprising measuring a differential response in an electrical property of the at least one of the plurality of graphene varactors due to the binding of one or more analytes present in the gaseous sample.

8. The method of claim 7, the electrical property selected from the group consisting of capacitance or resistance.

9. The method of claim 6, wherein the self-assembled monolayer provides a Langmuir theta value of at least 0.9.

\* \* \* \* \*